(12) United States Patent
Najar

(10) Patent No.: US 11,083,450 B2
(45) Date of Patent: Aug. 10, 2021

(54) LAPAROSCOPIC DEVICE

(71) Applicant: LAPROTECH AB, Västerås (SE)

(72) Inventor: Azad Najar, Västerås (SE)

(73) Assignee: LAPROTECH AB, Västerås (SE)

( * ) Notice: Subject to any disclaimer, the term of this patent is extended or adjusted under 35 U.S.C. 154(b) by 121 days.

(21) Appl. No.: 16/308,704

(22) PCT Filed: Jun. 9, 2017

(86) PCT No.: PCT/EP2017/064160
§ 371 (c)(1),
(2) Date: Dec. 10, 2018

(87) PCT Pub. No.: WO2017/212040
PCT Pub. Date: Dec. 14, 2017

(65) Prior Publication Data
US 2019/0142414 A1    May 16, 2019

(30) Foreign Application Priority Data

Jun. 10, 2016  (SE) .................................... 1650819-4
Aug. 22, 2016  (SE) .................................... 1651125-5

(51) Int. Cl.
*A61B 17/04*       (2006.01)
*A61B 17/062*      (2006.01)
(Continued)

(52) U.S. Cl.
CPC ........ *A61B 17/0469* (2013.01); *A61B 17/062* (2013.01); *A61B 17/0487* (2013.01);
(Continued)

(58) Field of Classification Search
CPC ...... A61B 17/00234; A61B 2017/2944; A61B 2017/2919; A61B 2017/06057;
(Continued)

(56) References Cited

U.S. PATENT DOCUMENTS 4,597,390 A   7/1986  Mulhollan et al.
5,364,365 A  11/1994  Wortrich
(Continued)

FOREIGN PATENT DOCUMENTS

CN   103379865 A   10/2013
DE       9112301 U1  11/1991
(Continued)

OTHER PUBLICATIONS

International Search Report and Written Opinion dated Oct. 27, 2017 by the International Searching Authority for Patent Application No. PCT/EP2017/064160, which was filed on Jun. 9, 2017 and published as WO 2017/212040 dated Dec. 14, 2017 (Inventor—Azad Najar; Applicant—Laprotech AB) (14 pages).

*Primary Examiner* — Richard G Louis
(74) *Attorney, Agent, or Firm* — Ballard Spahr LLP

(57) ABSTRACT

A laparoscopic device (10) comprising a handle assembly (30) by which the user may hold the laparoscopic device (30); and a tool gripping assembly (60) which holds a tool member (20) is disclosed. The tool gripping assembly (60) comprises a longitudinally extending rod (70) having a longitudinal axis A, a distal end (71) and a proximal end (72) The proximal end (72) is configured to be attached to the handle assembly (30), said distal end (71) is provided with a holding member (73) capable of holding a tool member (20). The tool gripping assembly (60) further comprises a first sleeve (80) partially surrounding and being longitudinally and independently displaceable parallel to the longitudinal axis A along an outer surface of said longitudinally extending rod (70), and a second sleeve (90) partially surrounding and being longitudinally and independently displaceable parallel to the longitudinal axis A along an outer surface of said first sleeve (80). The first and second sleeves (80, 90) are longitudinally displaceable in relation to each other and said longitudinally extending rod (70), and
(Continued)

are configured to clamp said tool member (20) to said holding member (73) in a variable angle α in relation to said longitudinal axis A, wherein said variable angle α depends on the relative positions of the first and second sleeves (80, 90) to the longitudinally extending rod (70).

19 Claims, 16 Drawing Sheets

(51) Int. Cl.
  *A61B 17/06* (2006.01)
  *A61B 17/29* (2006.01)
  *A61B 17/00* (2006.01)

(52) U.S. Cl.
  CPC ..... *A61B 17/29* (2013.01); *A61B 2017/00473* (2013.01); *A61B 2017/06057* (2013.01); *A61B 2017/2912* (2013.01); *A61B 2017/2919* (2013.01); *A61B 2017/2927* (2013.01); *A61B 2017/2944* (2013.01)

(58) Field of Classification Search
  CPC ...... A61B 17/0487; A61B 2017/00473; A61B 17/29; A61B 2017/2912; A61B 17/0469
  See application file for complete search history.

(56) References Cited

U.S. PATENT DOCUMENTS

| | | | | |
|---|---|---|---|---|
| 5,376,096 | A | * | 12/1994 | Foster ................ A61B 17/0469 606/147 |
| 6,102,920 | A | * | 8/2000 | Sullivan ............... A61B 17/062 606/147 |
| 2004/0249394 | A1 | * | 12/2004 | Morris ............... A61B 17/0469 606/144 |
| 2012/0165838 | A1 | | 6/2012 | Kobylewski |
| 2016/0345995 | A1 | | 12/2016 | Takei |

FOREIGN PATENT DOCUMENTS

| | | |
|---|---|---|
| EP | 0634143 | 1/1995 |
| JP | 2000139931 A | 5/2000 |
| WO | WO-1993/021833 A1 | 11/1993 |
| WO | WO-1999/055217 A1 | 11/1999 |
| WO | WO-2014/145724 A2 | 9/2014 |
| WO | WO-2015/122353 A1 | 8/2015 |

* cited by examiner

LAPAROSCOPIC DEVICE

CROSS-REFERENCE TO RELATED APPLICATIONS

This application is a U.S. National Phase Application of International Application No. PCT/EP2017/064160, filed Jun. 9, 2017, which claims priority to Swedish Patent Application Nos. SE 1650819-4, filed Jun. 10, 2016, and SE 1651125-5, filed Aug. 22, 2016, each of which are hereby incorporated by reference in their entirety.

TECHNICAL FIELD

The present application relates to a laparoscopic device which enables a tool member held therewith to be used at fixed or variable angles during surgical procedures.

BACKGROUND OF THE INVENTION

During laparoscopic surgery operations are performed far from their location through small incisions (usually 0.5-1.5 cm) elsewhere in the body. There are a number of advantages to the patient with laparoscopic surgery versus the more common, open procedure. Pain and hemorrhaging are reduced due to smaller incisions and recovery times are shorter.

During laparoscopic surgery the key element is the use of a laparoscope, a long fiber optic cable system which allows viewing of the affected area by snaking the cable from a more distant, but more easily accessible location. As the surgery is performed at a distance, instruments with long handles are used in order to perform all steps of the operation. In laparoscopic procedures a plurality of tubular members e.g. trocars may be inserted through offset incisions and advanced proximal to the tissue site of interest. The tubular members utilized are relatively rigid and of a diameter sufficient to facilitate the passage of a variety of devices there through, including for example gas inflation conduits, electrosurgical devices, imaging apparatuses, forceps, scissors, probes, dissectors, hooks, retractors and suturing devices.

An important step in laparoscopic surgery is to effectively suture an internal tissue site of interest. Such suturing entails the passage of suture material into and back out of the tissue at least once and most typically a plurality of times followed by the provision of a knot adjacent to the sutured tissue.

Although laparoscopic surgery provides many advantages one of the disadvantages is that sometimes the surgeon has limited range of motion due to limited space at the surgical site, which results in a loss of dexterity. Under certain circumstances the available space at the surgical site is so restricted that suturing tissues together using a regular laparoscopic instrument becomes very difficult. In these situations the suturing procedure may be improved by changing the angle of the needle or thread to be able to reach and suture tissues together at narrow sites. Adjusting the angle of the needle is currently achieved by means of forceps which grip the needle at the desired angle. A first pair of forceps holds on to the needle while a second pair grips the needle at the correct angle required for suturing. However, once the second pair of forceps has gripped the needle at a certain angle there is no way to adjust the angle unless the first pair of forceps again grips the needle and adjusts the angle. This may be a cumbersome procedure before the correct angle for the needle is obtained.

SUMMARY OF THE INVENTION

Viewed from a first perspective, the present teachings provide a laparoscopic device wherein the user is able to manipulate an attached tool member without the need for additional instruments such as e.g. forceps. The laparoscopic device as described herein can be used when there is a need to adjust e.g. a suturing tool member to an exact angle at the surgical site without the use of additional forceps or other instruments.

This may be is achieved by a laparoscopic device comprising a handle assembly by which the user may hold the instrument, and a tool gripping assembly which grips and holds on to a tool member. The tool gripping assembly comprises a longitudinally extending rod having a longitudinal axis A, a distal end and a proximal end. The proximal end of the longitudinally extending rod is configured to be attached to the handle assembly and said distal end is provided with a holding member capable of gripping and holding a tool member. The tool gripping assembly further comprises a first sleeve partially surrounding and being longitudinally and independently displaceable parallel to the longitudinal axis A along an outer surface of said longitudinally extending rod, and a second sleeve partially surrounding and being longitudinally and independently displaceable parallel to the longitudinal axis A along an outer surface of said first sleeve. Said first and second sleeves are longitudinally displaceable in relation to each other and said longitudinally extending rod, and are configured to clamp said tool member to said holding member into a variable angle $\alpha$ in relation to said longitudinal axis A. Said variable angle $\alpha$ depends on the relative positions of the first and second sleeves to the longitudinally extending rod.

The tool member can be a suture needle having a first end provided with a piercing tip, a second end opposite to the first end and a mid-portion. The mid-portion of the one or more tool members may have a square or rectangular cross section. A square cross section prevents rotation of the tool member(s) when clamped against the holding member. The square or rectangular mid-portion of the tool member is configured to fit into the holding member at the distal end of the longitudinally extending rod. In other embodiments the holding member may also grip and hold a suturing thread.

The handle assembly is designed to be held by the user during use and comprises an actuation lever, and a housing, said housing comprising a spring and a slider.

The actuation lever is articulated to the first and second sleeves via a first and a second linking arm and a slider. Said first and second linking arms each have a first and a second end, wherein the first end of the first linkage arm is connected to the slider located inside the housing. The second end of the first linkage arm is connected to the first end of the second linkage arm by means of a sliding pin slidably coupled in a slit in the actuation lever, and the second end of the second linkage arm is connected to the housing.

The actuation lever has two working positions; the tool rotating position and the tool clamping position.

In the tool rotating position the longitudinally extending rod may be rotated around the longitudinal axis A in both the clockwise and the counter clockwise direction. Rotation of the longitudinally extending rod rotates also the tool member, thereby enabling the user to place the tool member in the optimal position at the surgical site in relation to the handle assembly.

In the tool clamping position the actuation lever is configured to slidably displace the first and second sleeves simultaneously along the longitudinally extending rod and parallel to the longitudinal axis A. By pressing the actuation lever all the way towards the housing, the sliding pin which connects the second end of the first linkage arm to the first end of the second linkage arm, slides in the slit towards the proximal end of the handle assembly and pushes the slider inside the housing towards the distal end of the laparoscopic device. The slider is inside the housing connected to both the first and the second sleeves and pushes both the first and the second sleeves towards the distal end of the laparoscopic device when the actuation is pressed towards the housing. In the tool clamping position the longitudinally extending rod remains firmly in position and is unable to rotate.

The laparoscopic device further comprises a tool angle adjusting assembly configured to slidably displace the second sleeve in relation to the first sleeve and the longitudinally extending rod parallel to the longitudinal axis A when said tool angle adjusting assembly is rotated. By rotating a second tool angle adjusting member of the tool angle adjusting assembly, only the second sleeve is displaced. The second sleeve is displaced independently of the longitudinally extending rod and the first sleeve. Rotation of the second tool angle adjusting member varies the angle $\alpha$ of the tool member in relation to the longitudinally extending rod. The longitudinally extending rod remains firmly in position and is unable to rotate also during the rotation of the tool angle adjusting member.

The first sleeve has a distal end and a proximal end, said proximal end is configured to be attached to the handle assembly, and said distal end is provided with a first notch configured to receive the mid-portion of the tool member. The first notch has a first length extending parallel to the longitudinal axis A and in one embodiment the width of the first notch matches the width of the square cross section at the tool member mid-portion. Alternatively the width of the first notch may also be wider than the cross section of the tool member mid-portion and extend around substantially half of the circumference of the first sleeve.

The second sleeve has a distal end and a proximal end. Said proximal end is configured to be attached to the tool angle adjusting member, and said distal end is provided with a second notch and a third notch. The second and third notches are configured to receive the mid-portion of the tool member. The second notch has a second length extending parallel to the longitudinal axis A. The third notch has a third length extending parallel to the longitudinal axis A and in one embodiment the widths of the second and third notches match the width of the square cross section at the needle member mid-portion. Alternatively the widths of the second and third notches may also be wider than the cross sections of the tool member mid-portion and extend around substantially half of the circumferences of the second sleeve.

The second notch is positioned opposite said third notch along a circumference of the second sleeve distal end, and the second notch on the second sleeve distal end is aligned with the first notch on the first sleeve distal end.

The first notch on the first sleeve is longer than the second notch on the second sleeve and the third notch on the second sleeve is longer than the first notch on the first sleeve.

When said tool member is clamped to said holding member by slidably displacing said first and second sleeves longitudinally and parallel to said longitudinal axis A in relation to each other and said longitudinally extending rod, said mid-portion of the tool member is positioned in at least one or more of the first, second and third notches, thereby placing said tool member into varying angles $\alpha$ in relation to said longitudinal axis A.

By slidably displacing said first and second sleeves longitudinally and parallel to said longitudinal axis A in relation to each other and said longitudinally extending rod the angle $\alpha$ of the tool member may be varied between 30° to 150°, such as between 40° to 140°, such as between 50° to 130° in relation to said longitudinal axis A.

Viewed from a second perspective, the present teachings can provide a laparoscopic device wherein the user is able to manipulate the attached tool member without the need for additional instruments such as e.g. forceps. The laparoscopic device as described herein can be used when there is a need to use a suturing needle having a fixed angle at the surgical site. In a further embodiment this may be achieved by a laparoscopic device comprising a handle assembly by which the user may hold the laparoscopic device, and a tool gripping assembly which holds one or more tool members. The tool gripping assembly comprises a longitudinally extending rod having a longitudinal axis A, a distal end and a proximal end. The proximal end is configured to be attached to the handle assembly and the distal end is provided with one or more holding members capable of holding the one or more tool members. The tool gripping assembly further comprises a sleeve partially surrounding and being longitudinally and independently displaceable parallel to the longitudinal axis A along an outer surface of said longitudinally extending rod. The sleeve has a distal end provided with one or more notches with different lengths. The notches may have edges cut at an angle $\delta$ wherein said edges are configured to abut and clamp said one or more tool members to said one or more holding members at a fixed angle $\delta$ in relation to said longitudinal axis A.

The one or more tool members can be a suture needle having a first end provided with a piercing tip, a second end opposite to the first end and a mid-portion there between. In one embodiment the mid-portion of the one or more tool members has a square or rectangular cross section. A square cross section prevents rotation of the tool member(s) when clamped against the holding member. The square or rectangular mid-portion of the one or more tool members is configured to fit into the one or more holding members at the distal end of the longitudinally extending rod. The second end of the suturing needle may be provided with a suturing thread.

The handle assembly is designed to be held by the user during use of the instrument and comprises an actuation lever and a housing, wherein said housing comprises a spring and a slider.

The actuation lever is articulated to the sleeve via a first and a second linking arm and a slider. The first and second linking arms each have a first and a second end, and wherein the first end of the first linkage arm is connected to the slider, the second end of the first linkage arm is connected to the first end of the second linkage arm by means of a sliding pin slidably coupled in an actuation lever slit arranged in the actuation lever, and the second end of the second linkage arm is connected to the housing.

The actuation lever has two working positions; the tool rotating position and the tool clamping position.

In the tool rotating position the longitudinally extending rod may be rotated around the longitudinal axis A in both the clockwise and the counter clockwise direction. Rotation of the longitudinally extending rod rotates also the one or more tool members thereby enabling the user to place the one or more tool members in the optimal position at the surgical site in relation to the handle assembly.

In the tool clamping position the actuation lever is configured to slidably displace the sleeve parallel to the longitudinal axis A along the longitudinally extending rod and clamp the one or more tool members into said one or more holding members.

When the actuation lever is pressed all the way towards the housing, i.e. to the tool clamping position, said slider is configured to slidably displace the sleeve parallel to the longitudinal axis A and along the longitudinally extending rod. By pressing the actuation lever towards the housing the sliding pin which connects the second end of the first linkage arm to the first end of the second linkage arm slides in the slit towards the proximal end of the handle assembly and pushes the slider inside the housing towards the distal end of the laparoscopic device. The slider located inside the housing is connected to the sleeve and pushes the sleeve towards the distal end of the laparoscopic device.

The sleeve has a distal end and a proximal end. Said proximal end is configured to be attached to the handle assembly and said distal end is provided with one or more notches having edges cut at an angle δ which are configured to receive and abut the mid-portion of the one or more tool members. The one or more notches each have a length extending parallel to the longitudinal axis A. In one embodiment the widths of the one or more notches extend around substantially half of the circumference of the sleeve.

The edges of the one or more notches are cut at an angle δ such that when said edges abut the mid-portions of the one or more tool member to the cleft, the one or more tool members are clamped at a fixed angle δ parallel to the cut edges of the one or more notches.

The distal end of the longitudinally extending rod is provided with one holding member capable of holding one tool member at a fixed angle δ.

The distal end of the longitudinally extending rod is provided with two holding members capable of holding two tool members at a fixed angle δ.

The distal end of the laparoscopic device may be flexible.

Definitions

In the present disclosure, when the term distal end is used this refers to the part or end of the device which is located closest to the patient when in use. Correspondently the term "proximal end" is used it is intended to mean the part or end of the device which is located farthest away from the patient during use.

DETAILED DESCRIPTION

Figure 1:
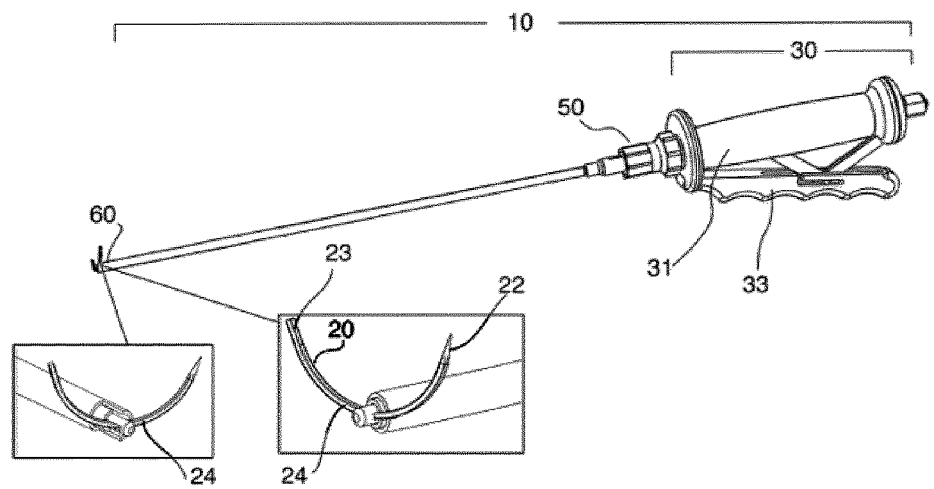
FIG. 1 is a view of a laparoscopic instrument holding a tool member

FIG. 1 is a view of the laparoscopic device 10 holding a tool member 20. The laparoscopic device 10 comprises a handle assembly 30 by which the user may hold the device 10, a tool angle adjusting assembly 50, and a tool gripping assembly 60 which grips a tool member 20. In the illustrated embodiments the tool member 20 is a curved or straight suturing needle. However, it is also contemplated that the tool member 20 may be forceps, scissors, probes, dissectors, hooks or retractors. In some embodiments the laparoscopic device 10 may also be used for gripping and handling suture threads.

Figure 2A:
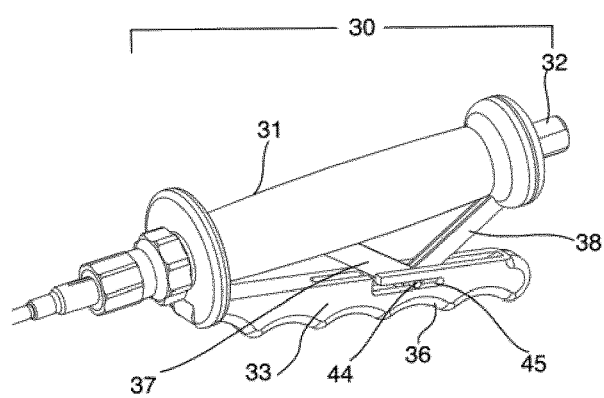
FIGS. 2A and B are views of the handle assembly and the tool angle adjusting assembly
Figure 2B:
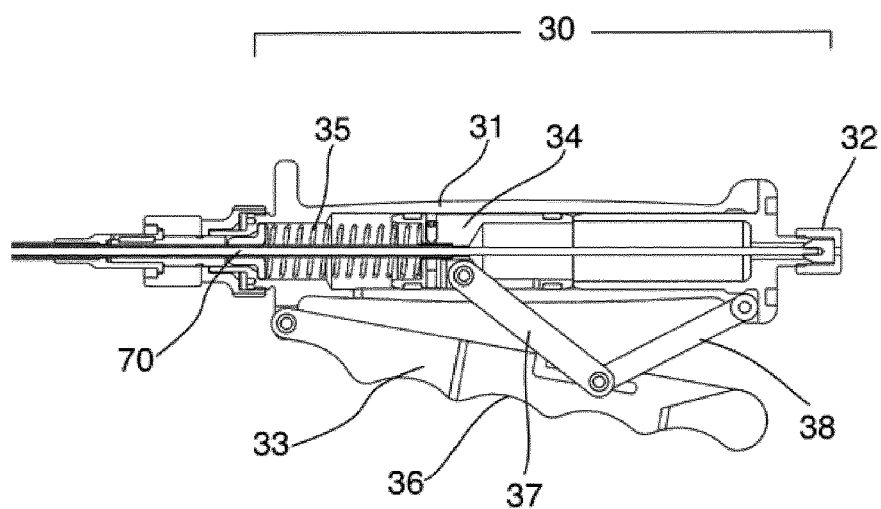

The handle assembly 30 comprises a housing 31 and an actuation lever 33 (FIGS. 2A, 2B). The handle assembly 30 is designed to be held by one hand (left or right) by gripping around the housing 31 and the actuation lever 33. The housing 31 comprises a slider 34 and a spring 35 (FIG. 2B) and the actuation lever 33 can be provided with a finger grip 36 to enable safe and precision handling of the laparoscopic device 10.

Figure 3:
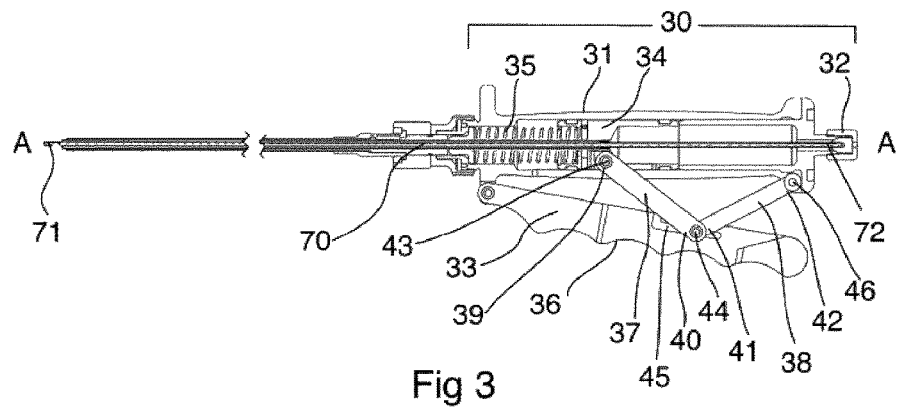
FIG. 3 is a cross sectional view of the laparoscopic instrument including the distal end of the gripping assembly FIGS. 4A and B are detailed views of the holding member at the distal end of the longitudinally extending rod (A) and an alternative embodiment (B).
Figure 4A:
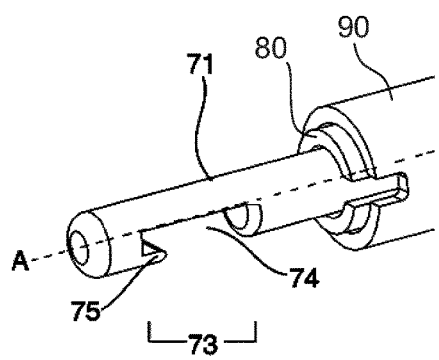
Figure 4B:
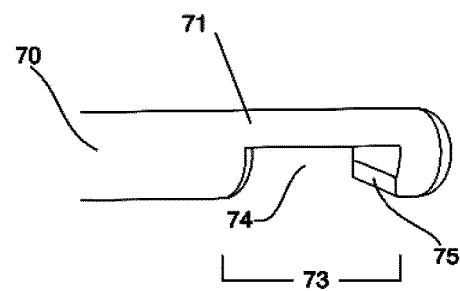

The tool gripping assembly 60 comprises a longitudinally extending rod 70 having a longitudinal axis A, a distal end 71 and a proximal end 72 (see FIGS. 3 and 4A). The longitudinal axis A extends along the longitudinally extending rod 70. The longitudinally extending rod distal end 71 is provided with a holding member 73 capable of holding a tool member 20. The holding member 73 is shaped as a hook comprising a cleft 74 into which the tool member 20 fits (see FIGS. 4A and B). The cleft 74 may have varying depths. In some embodiments the cleft 74 may be shallow providing only a narrow ledge 75 that will retain the tool member 20 (see FIG. 4B). In other embodiments the cleft 74 may be deep providing a firm containment of the tool member 20 (see FIG. 4A).

Figure 15A:
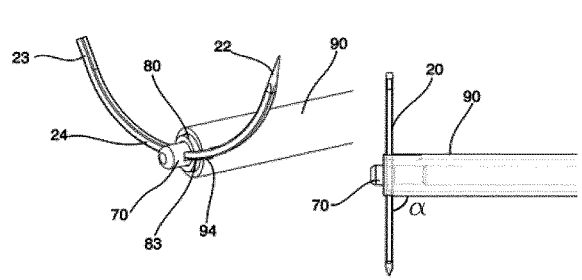

In the illustrations the tool member 20 is a curved or straight suture needle having a first end provided with a piercing tip 22, a second end 23 opposite the first end 22, and a mid-portion 24 (as illustrated in FIGS. 1, 15A,B, 16A,B, and 17A,B). In one embodiment the mid-portion 24 of the tool member 20 has a square or rectangular cross section configured to fit into the cleft 74 of the holding member 73 at the longitudinally extending rod distal end 71. A square or rectangular cross section prevents rotation of the tool member 20 when clamped against the holding member 73.

The longitudinally extending rod 70 extends from the distal end 71 of the laparoscopic device 10, through the tool angle adjusting assembly 50 and through the entire handle assembly 30 (see FIG. 3). At its proximal end 72 it is connected to a tool turning nut 32 arranged on the exterior of the handle assembly 30.

The tool gripping assembly 60 further comprises a first sleeve 80 partially surrounding and being longitudinally and independently displaceable parallel to the longitudinal axis A along the outer surface of said longitudinally extending rod 70 (see FIGS. 2B, 4A). The first sleeve 80 has an extension in its longitudinal direction which substantially exceeds its extension in the transverse direction. The longitudinal extension of the first sleeve 80 is at least 5 times, such as at least 10 times, such as more than 15 times longer than its transverse extension.

Figure 5A:
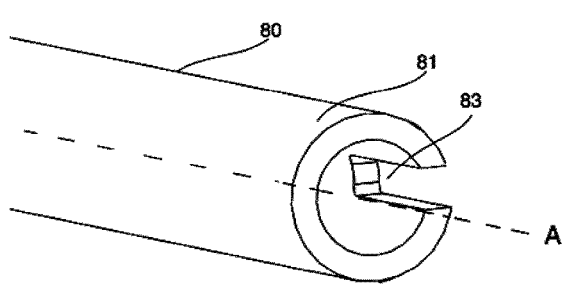
FIGS. 5A and B are detailed views of the distal end of the first notch on the first sleeve (A) and an alternative embodiment (B).
Figure 5B:
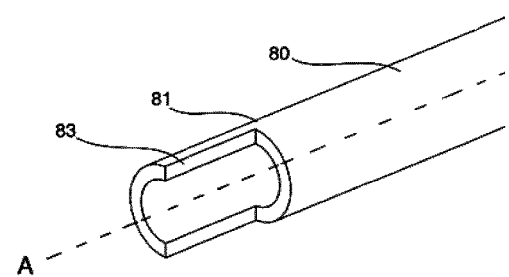
Figure 6:
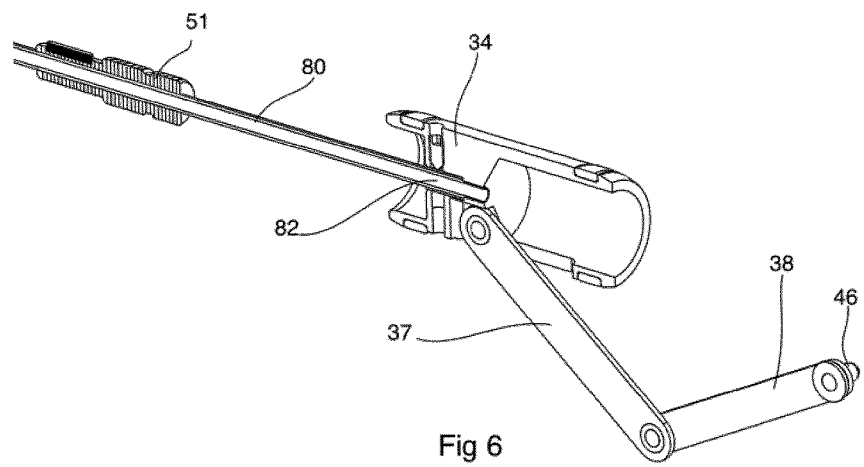
FIG. 6 is a cross sectional view of the handle assembly and the tool angle adjusting assembly

The first sleeve 80 has a distal end 81 and a proximal end 82 (see FIGS. 5A, 5B and 6). The first sleeve distal end 81 is provided with a first notch 83 configured to receive the mid-portion 24 of the tool member 20 (FIG. 5A). The first notch 83 has a first length extending parallel to the longitudinal axis A. In one embodiment the width of the first notch 83 matches the width of the square or rectangular cross section at the tool member mid-portion 24 (see FIG. 5A). In some embodiments the width of the first notch 83 extends around substantially half of the first sleeve 80 circumference (see FIG. 5B). The proximal end 82 of the first sleeve 80 is attached to a first tool angle adjusting member 51 in the tool angle adjusting assembly 50 and a slider 34 inside the housing 31 (see FIGS. 2, and 6) of the handle assembly 30 as explained further below.

A second sleeve 90 is partially surrounding and being longitudinally and independently displaceable parallel to the longitudinal axis A along the outer surface of said first sleeve 80 (see FIGS. 2B and 4A). The second sleeve 90 has an extension in its longitudinal direction which substantially exceeds its extension in the transverse direction. The longitudinal extension of the second sleeve 90 is at least 5 times, such as at least 10 times, such as more than 15 times longer than its transverse extension.

Figure 7A:
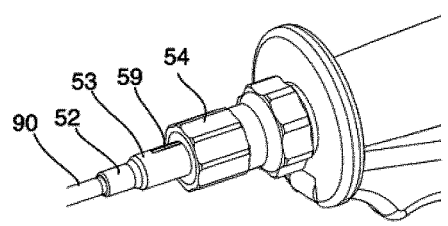
FIGS. 7A-C are detailed views of the tool angle adjusting assembly
Figure 7B:
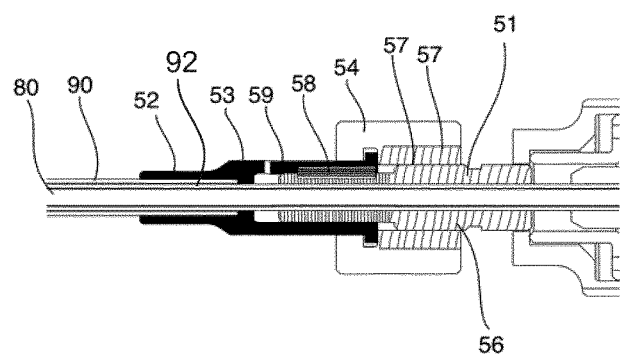
Figure 7C:
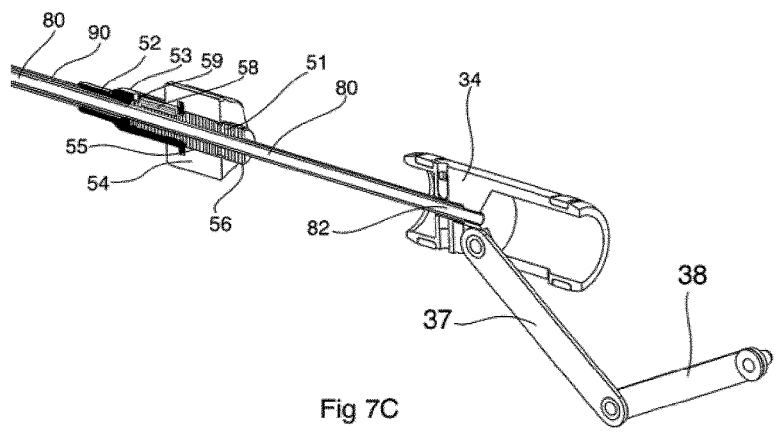
Figure 8:
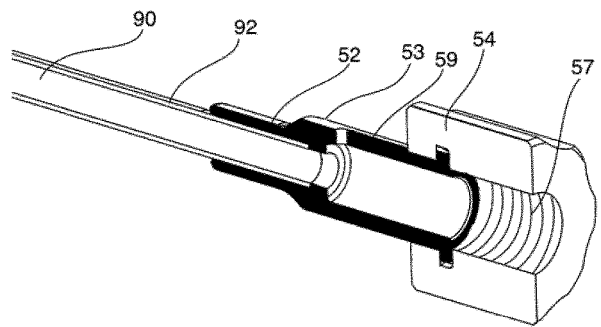
FIG. 8 is a cross sectional view of the proximal end of the second sleeve connecting to the tool angle adjusting assembly FIGS. 9A and B are detailed views of the distal end on the second sleeve showing a first embodiment (A) and a second embodiment (B).
Figure 9A:
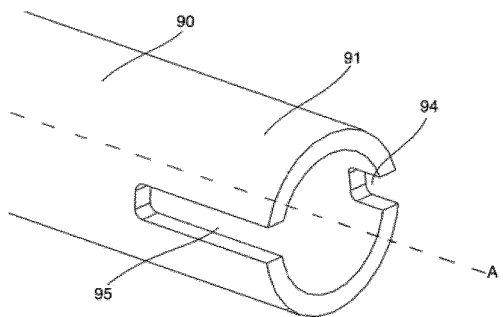

The second sleeve 90 has a distal end 91 and a proximal end 92 (see FIGS. 8, 9A and B). Said proximal end 92 is attached to a second tool angle adjusting member 52 in the tool angle adjusting assembly 50 (see FIGS. 7A, 7B, 7C and 8) as explained further below. The distal end 91 of the second sleeve 90 is provided with a second notch 94 and a third notch 95 (see FIGS. 9A, 4A). The second and third notches 94, 95 are configured to receive the mid-portion 24 of the tool member 20.

Figure 9B:
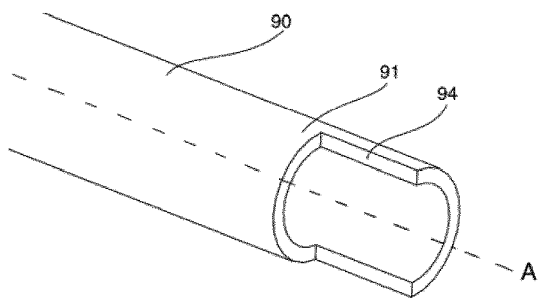

The second notch 94 has a second length extending parallel to the longitudinal axis A. The third notch 95 has a third length extending parallel to the longitudinal axis A (see FIGS. 5A, and 9A). In one embodiment the widths of the second and third notches 94, 95 match the width of the square or rectangular cross section of the tool member mid-portion 24. In an alternative embodiment the distal end 91 of the second sleeve 90 is provided with only a second notch 94. In this embodiment the width of the second notch 94 extends around substantially half of the second sleeve circumference (see FIG. 9B).

As seen in FIG. 9A the second notch 94 is positioned opposite said third notch 95 along a circumference of the second sleeve 90, and the second notch 94 on the second sleeve 90 is aligned with the first notch 83 on the first sleeve 80 (see FIGS. 4A, 5A, and 9A). The first length of the first notch 83 on the first sleeve 80 is longer than the second length of the second notch 94 on the second sleeve 90, and the third length of the third notch 95 on the second sleeve 90 is longer than the length of the first notch 83 on the first sleeve 80. The reason for this will explained further below.

Said first and second sleeves 80, 90 are longitudinally displaceable parallel to the longitudinal axis A in relation to each other and the longitudinally extending rod 70. This means that each one of the sleeves 80, 90 is displaceable independently of the other in either the proximal or the distal direction parallel to the longitudinal axis A. The first and second sleeves 80, 90 are also displaceable longitudinally in relation to the longitudinally extending rod 70.

The first and second sleeves 80, 90 are configured to clamp said tool member 20 to the holding member 73 arranged at the distal end of the longitudinally extending rod 70 into a variable angle $\alpha$ in relation to said longitudinal axis A. Said variable angle $\alpha$ depends on the relative positions of the first and second sleeves 80, 90 to the longitudinally extending rod 70.

The laparoscopic device 10 as described herein is operated by means of the actuation lever 33 and the tool angle adjusting assembly 50. The laparoscopic device 10 has four operating modes: the resting mode, the tool clamping mode, the tool rotating mode and the tool angle adjusting mode. The different operating modes of the laparoscopic device 10 will now be explained in detail.

Figure 10:
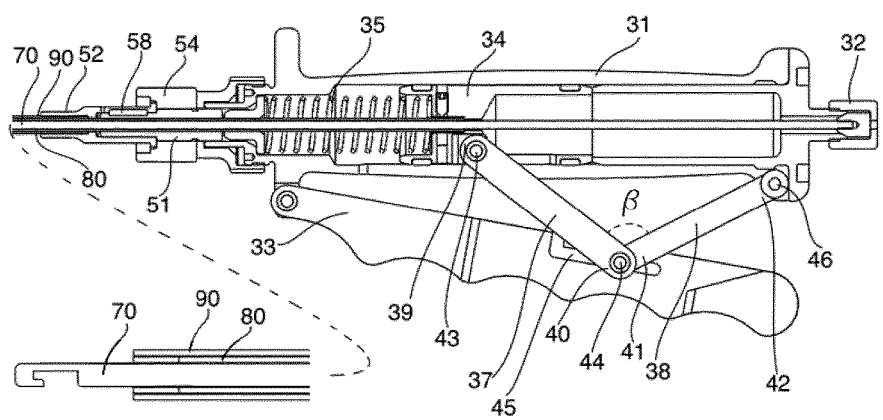
FIG. 10 is a cross sectional view of the laparoscopic instrument in a relaxed mode

When not in use the laparoscopic device 10 is in a relaxed mode (see FIG. 10). In the relaxed mode the second end 40 of the first linking arm 37 is connected to the first end 41 of the second linking arm 38 forming a slightly obtuse angle $\beta$ between the first and second linking arms 37, 38. In the relaxed mode the first and second sleeves 80, 90 have been displaced in the proximal direction from the holding member 73 leaving the cleft 74 in an open position arranged to receive the tool member 20 (see insert in FIG. 10).

However, when a user of the laparoscopic device 10 presses the actuation lever 33 towards the housing 31 the actuation lever 33 may reach three different working modes; the tool clamping mode, the tool angle adjusting mode or the tool rotating mode.

The Tool Clamping Mode

The actuation lever 33 which forms part of the handle assembly 30 is configured to slidably displace the first and second sleeves 80, 90 simultaneously and parallel to the longitudinal axis A along the longitudinally extending rod 70. The actuation lever 33 is articulated to the first and second sleeves 80, 90 via a first and a second linking arm 37, 38 and a slider 34 (see FIGS. 1, 2A and 6). Said first and second linking arms 37, 38 each have a first and a second end 39, 40, 41, 42, wherein the first end 39 of the first linking arm 37 is articulated to the slider 34 located inside the housing 31. The first end 39 of the first linking arm 37 is mounted to the slider 34 by means of a first mounting pin 43 around which the first end 39 of the first linking arm 37 may articulate. The first and second linking arms 37, 38 are connected to each other by means of a sliding pin 44 slidably coupled in an actuation lever slit 45 on the actuation lever 33. The second end 42 of the second linking arm 38 is articulated to the housing 31 by means of a second mounting pin 46 around which the second end 42 of the second linking arm 38 may articulate.

Figure 11:
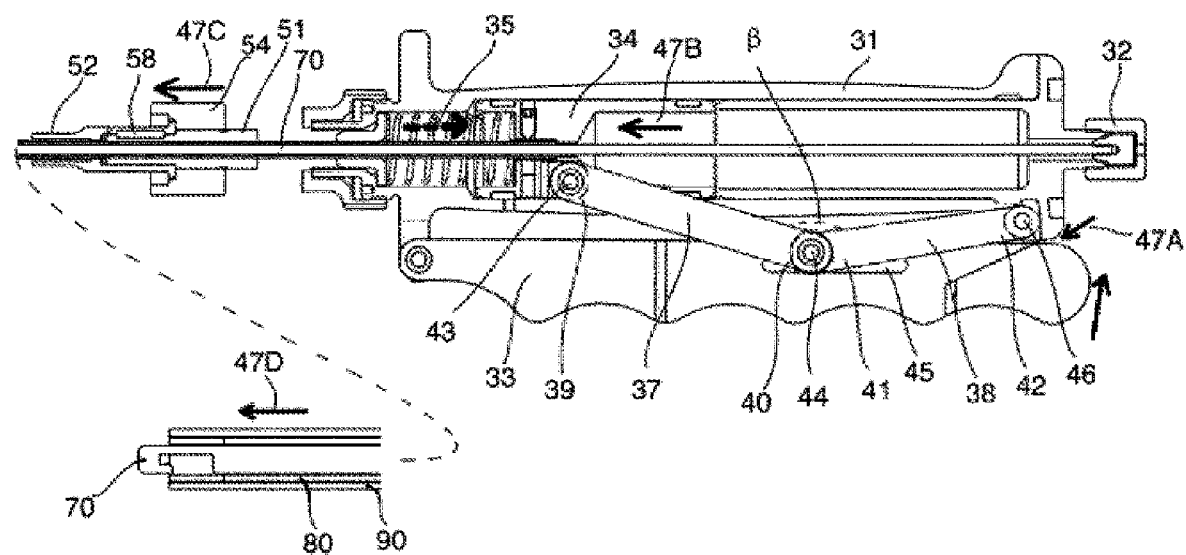
FIG. 11 is a cross sectional view of the laparoscopic instrument in a tool clamping mode FIGS. 12A and B are views showing the tool angle adjusting mode

The tool clamping mode is reached when the actuation lever 33 is pressed all the way towards the housing 31 such that the actuation lever 33 contacts the housing 31, (see arrow 47A in FIG. 11). In this mode the sliding pin 44 slides towards the distal end of the handle assembly 30, increasing the obtuse angle β between the first and second linking arms 37, 38, and thereby pushing the slider 34 towards the distal end of the handle assembly 30 (see arrow 47B in FIG. 11). The slider 34 is resiliently biased towards the proximal end of the housing 31 by means of a spring 35 (see dashed arrow in FIG. 11). The longitudinally extending rod 70 remains firmly in position and is unable to rotate in the tool clamping mode.

As explained above the first sleeve 80 is fixedly attached to the first tool angle adjusting member 51 which surrounds parts of the first sleeve 80 as it extends through the tool angle adjusting assembly 50. The proximal end 82 of the first sleeve 80 is fixedly attached to the slider 34 inside the housing 31 of the handle assembly 30 (see FIGS. 2A, 6 and 11). The second sleeve 90 is fixedly attached to the neck member 53 and the tool angle adjusting nut 54 which in turn is connected to the first tool angle adjusting member 51 by means of the screw thread (see FIGS. 2A, 8 and 7B).

Thus, when the actuation lever 33 is pressed towards the housing 31 (FIG. 11) and the slider 34 moves towards the distal end of the handle assembly 30 (see arrow 47B in FIG. 11), both the first and second sleeves 80, 90 together with the neck member 53 connected to the tool angle adjusting nut 54, which in turn is screwed to the first tool angle adjusting member 51, are slidably displaced simultaneously along the longitudinally extending rod 70 and parallel to the longitudinal axis A in the distal direction away from the handle assembly 30 (see arrow 47C in FIG. 11) and may clamp a tool member in the cleft 74 of the holding member 73 (see arrow 47D in FIG. 11). The resilient spring 35 provides an opposing force (see dashed arrow in FIG. 11) when the actuation lever 33 is pressed towards the housing, and consequently the first and second sleeves 80, 90 move in the proximal direction towards the handle assembly 30 along the longitudinally extending rod 70 and parallel to the longitudinal axis A when the actuation lever 33 is released and the laparoscopic device 10 returns to its relaxed mode as seen in FIG. 10. Accordingly, the first and second sleeves 80, 90 may be displaced simultaneously along the longitudinally extending rod 70 and parallel to the longitudinal axis A by pressing or releasing the actuation lever 33 (FIG. 11).

Tool Angle Adjustment Mode

Figure 12A:
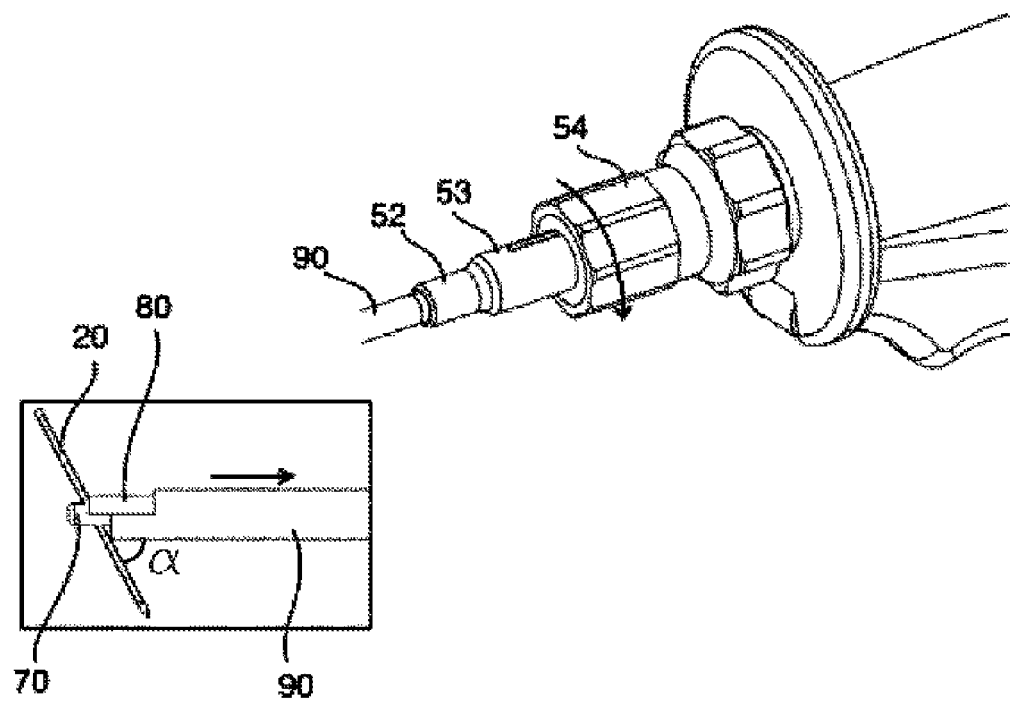
Figure 12B:
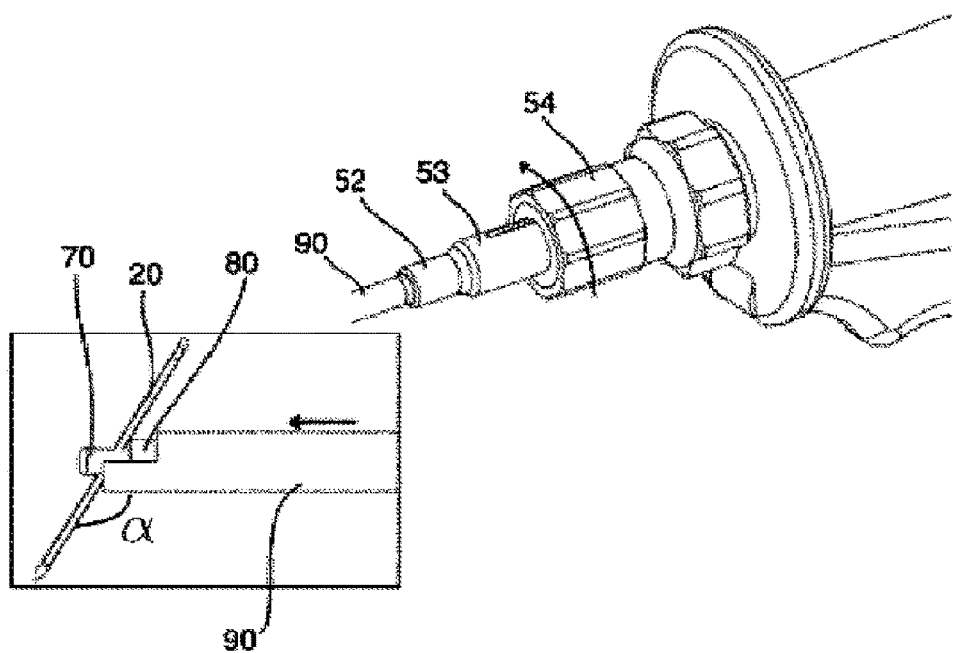

In the tool adjustment mode the angle α of the tool member 20 may be adjusted in relation to the longitudinally extending axis A. In the tool angle adjusting mode only the second sleeve 90 is displaced along the longitudinally extending rod 70 and parallel to the longitudinal axis A independently of the first sleeve 80, and the longitudinally extending rod 70 which remains firmly in position and is unable to rotate. This is accomplished by turning the tool angle adjusting nut 54 in the clockwise or counter clockwise directions (FIGS. 12A and 12B). By moving the second sleeve 90 independently from the first sleeve 80, the angle α of the tool member 20 may be varied in relation to the longitudinally extending axis A as will be explained further below.

The tool angle adjusting assembly 50 comprising a first tool angle adjusting member 51 and a second tool angle adjusting member 52, is arranged between the handle assembly 30 and the tool gripping assembly 60 (see FIGS. 1, 2A, 2B, 3, 12A and B). The tool angle adjusting assembly 50 enables angle adjustment of the tool member 20 in relation to the longitudinal axis A through independent displacement of the first and second sleeves 80, 90 parallel to the longitudinally extending axis A in relation to the longitudinally extending rod 70.

The first sleeve 80 is fixedly attached to the first tool angle adjusting member 51 which surrounds parts of the first sleeve 80 as it extends through the tool angle adjusting assembly 50 into the handle assembly 30 where it at its proximal end 82 is fixed to a slider 34 (see FIGS. 2A, 6, 7C).

The second sleeve 90 is at its proximal end 92 fixed to the second tool angle adjusting member 52 (see FIGS. 7B and 8). Said second tool angle adjusting member 52 comprises a neck member 53 connected to a tool angle adjusting nut 54. Said neck member 53 is fixedly attached to the proximal end 92 of the second sleeve 90 (see FIGS. 8 and 7B. The tool angle adjusting nut 54 surrounds said first tool angle adjusting member 51 and is rotatably connected thereto by means of a screw thread. The outer surface of the first tool angle adjusting member 51 is provided with an external screw thread 56, and the inner surface of the tool angle adjusting nut 54 is provided with an internal screw thread 57. A wedge 58 is fixedly attached to the first tool angle adjusting member 51 and protrudes into a slit 59 arranged on the second tool angle adjusting member 52. The wedge 58 prevents rotation of the second sleeve 90 when the second sleeve 90 is longitudinally and independently displaced parallel to the longitudinal axis A along the outer surface of said first sleeve 80.

By rotating the tool angle adjusting nut 54 in a clockwise or counter clockwise direction around the longitudinally extending axis A the second sleeve 90 is longitudinally and independently displaced parallel to the longitudinal axis A along the outer surface of said first sleeve 80 (see FIGS. 12A and 12B).

The Tool Rotating Mode

In the tool rotating mode the tool member 20 may be rotated around the longitudinal axis A. The tool rotating mode is reached when the actuation lever 33 is pressed only part of the distance towards the housing 31 (see arrow 48A in FIG. 13). The sliding pin 44 slides towards the proximal end of the handle assembly 30, and increases the obtuse angle β between the first and second linking arms 37, 38. In the tool rotating mode the longitudinally extending rod 70 is released from its firm and locked position and may now be rotated around its longitudinal axis A in both the clockwise and the counter clockwise direction (see FIG. 14). Rotation of the longitudinally extending rod 70 rotates also the one or more tool members 20 thereby enabling the user to place the one or more tool members 20 in the optimal position at the surgical site in relation to the handle assembly 30. This may be very advantageous when for example the operator wants to change position of the first end of the tool member e.g. 180° (i.e. flip the tool member to point in the opposite direction). By using the laparoscopic device 10 as described herein this rotational movement may be achieved without the use of any further tools.

The motions for adjusting the angle and position of the tool member 20 when placed in the tool gripping assembly 60 will now be described.

The tool member 20 is placed in the cleft 74 of the holding member 73. As discussed above the mid-portion 24 of the tool member 20 has in one embodiment a square or rectangular cross section designed to fit into the cleft 74 of the holding member 73 (See FIGS. 1, 4A, 15A and B, 16A and B, 17A and B). The tool member 20 is clamped into the cleft 74 of the holding member 73 by pressing the actuation lever 33 all the way towards the housing 31 thereby slidably displacing both of said first and second sleeves 80, 90 longitudinally and parallel to said longitudinal axis A in relation to each other and said longitudinally extending rod 70 towards the holding member 73 (see FIG. 11). As the first and second sleeves 80, 90 approach the holding member 73 the mid-portion 24 of the tool member 20 enters into one or more of the first, second and/or third notches 83, 94, 95, where after the tool member 20 becomes firmly clamped into the holding member 73 (see FIGS. 15A and B).

Figure 15B:
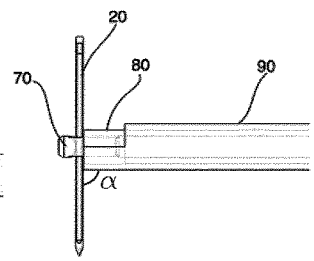

FIGS. 15A and B illustrate a tool member 20 which has been firmly clamped in the holding member 73 such that the tool member 20 forms an angle α of 90° in relation to the longitudinal axis A. FIG. 15B discloses the embodiment wherein the notches 83, 94 and 95 extend around half of circumference of the sleeves 80, 90.

When the tool member 20 is positioned at an angle of 90° in relation to the longitudinal axis A, both the first and second sleeves 80, 90 are pushed all the way towards the distal end 71 of the longitudinally extending rod 70. The first and second sleeves 80, 90 are aligned such that the mid-portion 24 of the tool member 20 is supported in the second notch 94 of the second sleeve 90 on a first side of the holding member 73 and abut to the distal end 81 of the first sleeve 80 on the opposite side of the holding member 73 (see FIG. 15A). In the illustrations the tool member 20 is a curved suturing needle.

The angle α between the tool member 20 and the longitudinal axis A may be altered by slidably displacing either the first 80 or the second sleeve 90, or both sleeves 80, 90 longitudinally and parallel to said longitudinal axis A in relation to each other and said longitudinally extending rod 70. By rotating the tool angle adjusting nut 54 in a clockwise or counter clockwise direction around the longitudinally extending axis A (see FIGS. 12A and 12B) the second sleeve 90 may be longitudinally and independently displaced parallel to the longitudinal axis A along the outer surface of said first sleeve 80 placing said mid-portion 24 of the tool member 20 in at least one or more of the first, second and third notches 83, 94, 95 (see FIGS. 4A and 5A, and 9A). The different lengths of the first, second and third notches 83, 94, 95 together with the individual displacements of the first and second sleeves 80, 90 in relation to each other and to the longitudinally extending rod 70 determine the angle α between the tool member 20 and the longitudinally extending axis A as described below.

Figure 16A:
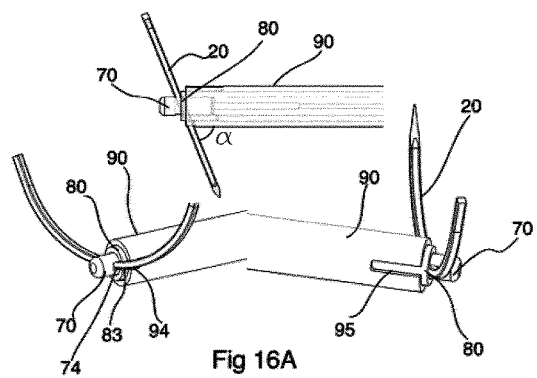
FIGS. 16A and B are detailed views of the tool gripping assembly holding the tool member at an angle of 70°
Figure 16B:
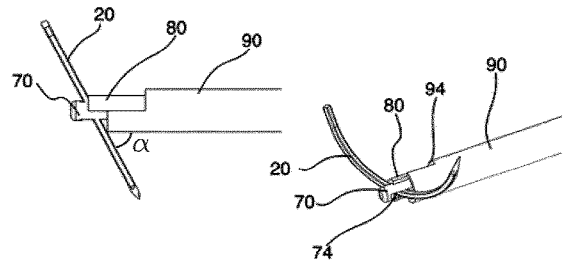

In FIGS. 16A and B the tool member 20 is positioned at an angle of about 70° to the longitudinally extending axis A. When placed at this angle the mid-portion 24 of the tool member 20 is supported in the first notch 83 of the first sleeve 80, and the second notch 94 on the second sleeve 90 on one side of the holding member 73 and abuts the distal end 81 of the first sleeve 80 on the opposite side of the holding member 73 (see FIG. 16A). FIG. 16B discloses the embodiment wherein the notches 83, 94 and 95 extend around half of circumference of the sleeves 80, 90.

Figure 17A:
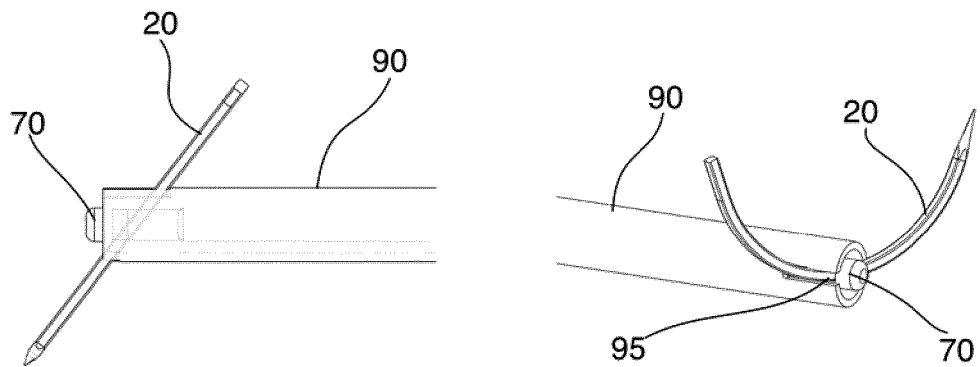
FIGS. 17A and B are detailed views of the tool gripping assembly holding the tool member at an angle of 130°
Figure 17B:
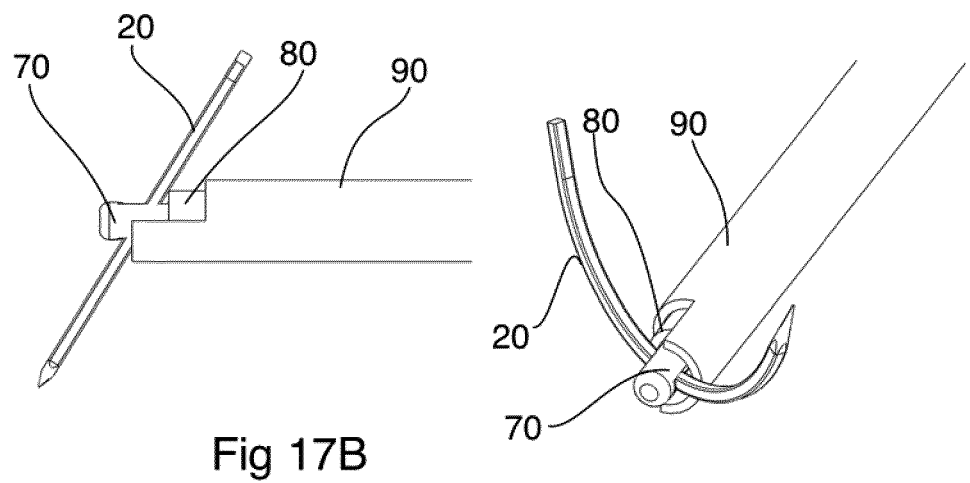

In FIGS. 17A and B the tool member 20 is placed at an angle of about 130° to the longitudinally extending axis A. When placed at this angle the mid-portion 24 of the tool member 20 is supported in the second notch 94 of the second sleeve 90 on one side of the holding member 73 and by the third notch 95 of the second sleeve 90 on the opposite side of the holding member 73 (see FIGS. 17A and B). When the tool member 20 is positioned at this obtuse angle α, the first sleeve 80 is withdrawn from the tool member 20 completely and the tool member mid-portion 24 is supported solely by the second and third notches 94, 95 in the second sleeve 90. FIG. 17B discloses the embodiment wherein the notches 83, 94 and 95 extend around half of circumference of the sleeves 80, 90.

By slidably displacing said first and second sleeves 80, 90 longitudinally and parallel to said longitudinal axis A in relation to each other and said longitudinally extending rod 70 as explained above, the angle of the tool member 20 may be varied between 30° to 150°, such as between 40° to 140°, such as between 50° to 130° in relation to said longitudinal axis A thereby facilitating surgery at narrow surgical sites.

Figure 13:
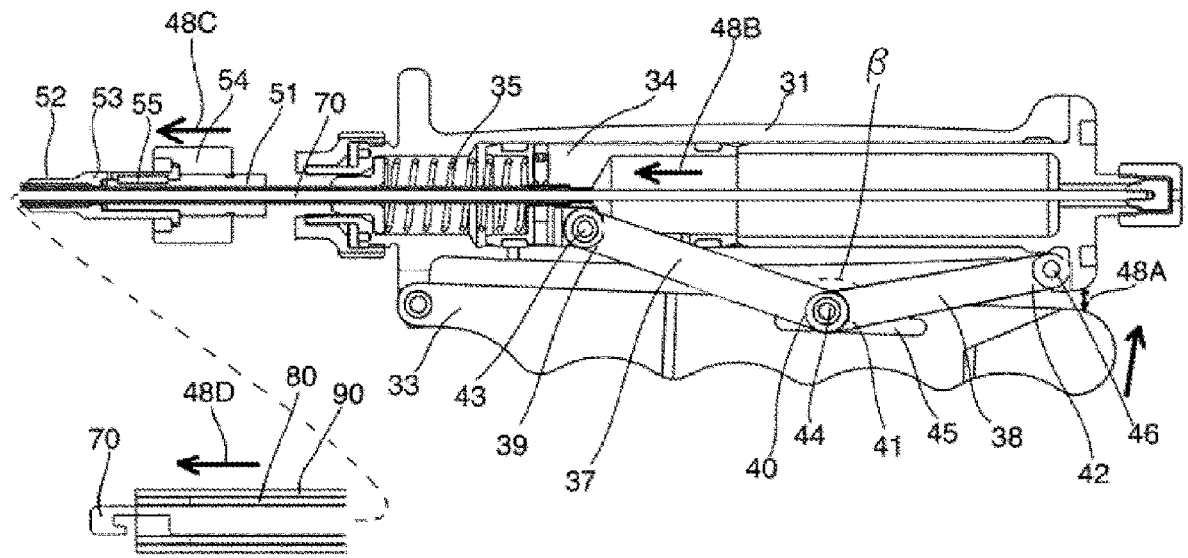
FIG. 13 is a cross sectional view of the laparoscopic instrument in a tool rotating view mode FIG. 14 discloses how the longitudinally extending rod is rotated in the tool rotating mode FIGS. 15A and B are detailed views of the tool gripping assembly holding the tool member at an angle of 90°
Figure 14:
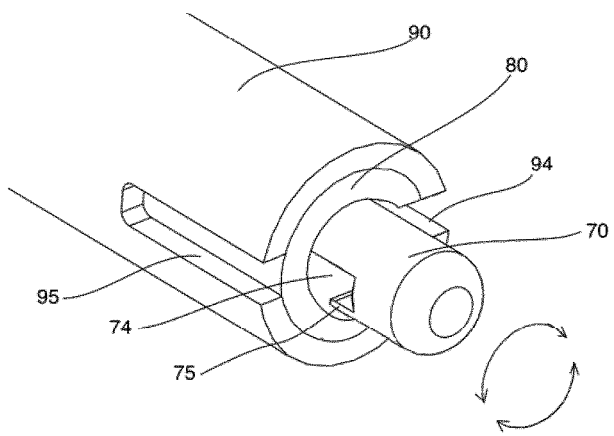

By pressing the actuation lever 33 only part of the distance towards the housing 31 the longitudinally extending rod 70 clamping the tool member 20 may be turned around the axis A (see FIGS. 13 and 14). This may be helpful in situations when e.g. the suture needle has to enter the tissue from the opposite direction. As soon as the actuation lever 33 is pressed firmly against the housing 31, the rotational movement of the longitudinally extending rod 70 around the longitudinal axis A stops and the position of the tool member 20 is fixed in relation to the longitudinal axis A.

Figure 18:
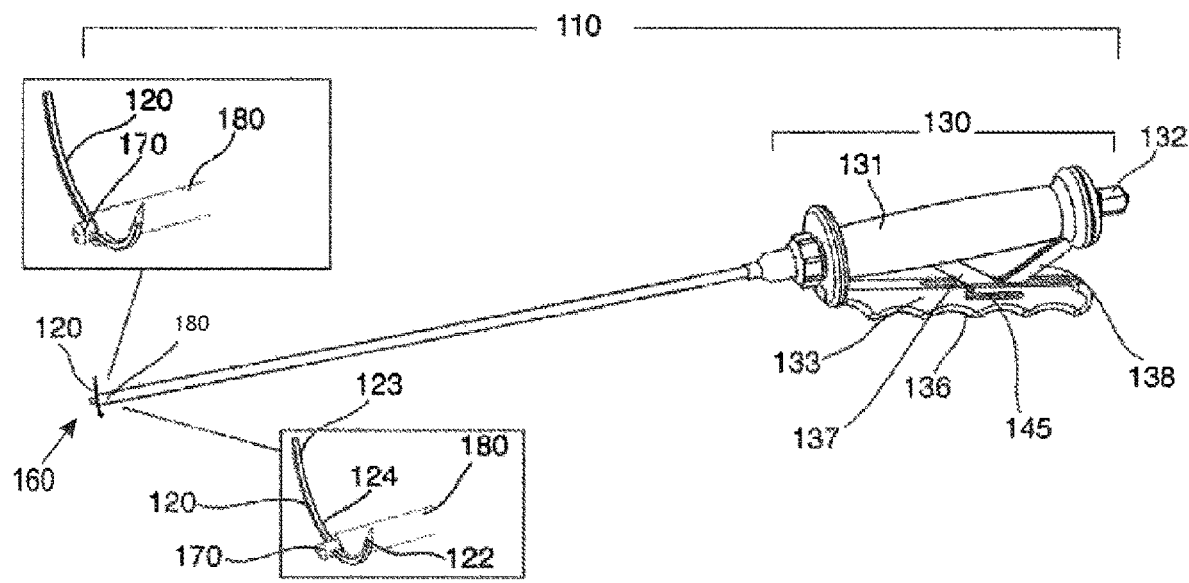
FIG. 18 is a view of an alternative laparoscopic device

FIG. 18 is a view of an alternative laparoscopic device 110 holding a tool member 120. The laparoscopic device 110 comprises a handle assembly 130 by which the user may hold the laparoscopic device 110, and a tool gripping assembly 160 which holds one or more tool members 120. In the illustrated embodiments the one or more tool members 120 is a curved suturing needle.

Figure 19A:
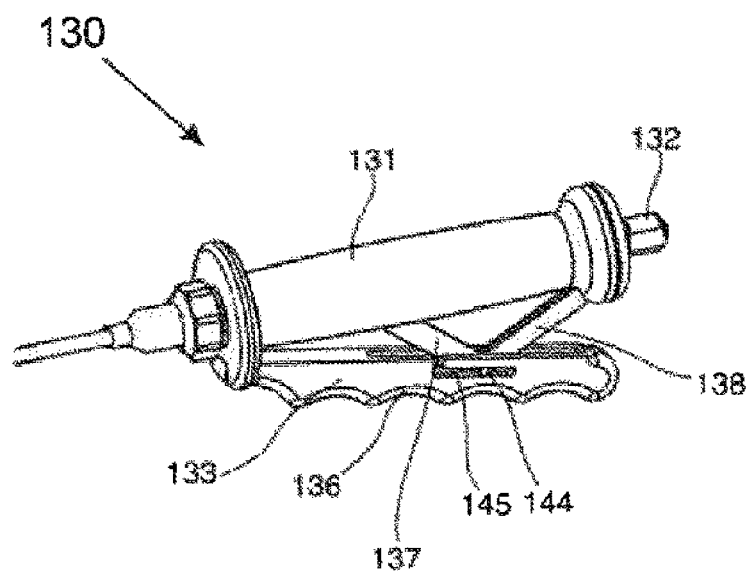
FIGS. 19A and B are views of the handle assembly and the tool angle adjusting assembly of the alternative laparoscopic device
Figure 19B:
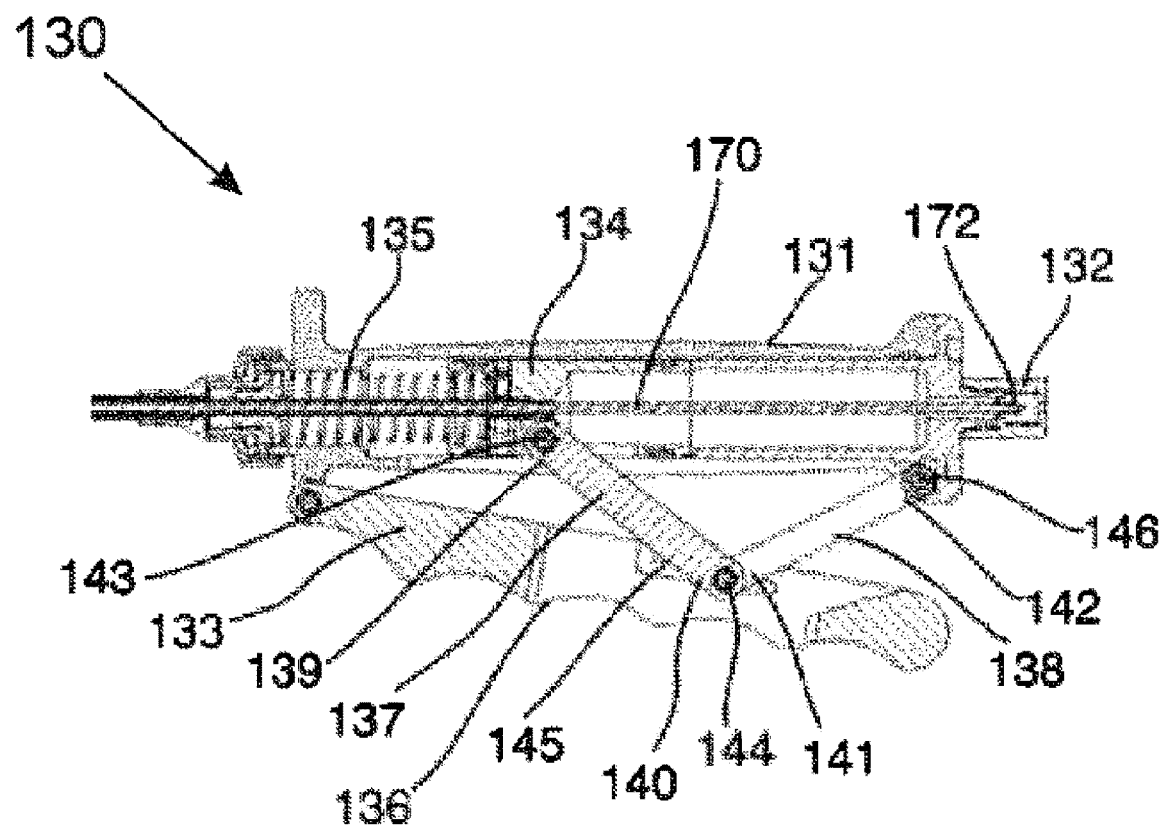

The handle assembly 130 comprises a housing 131 and an actuation lever 133 (FIGS. 19A and B). The handle assembly 130 is designed to be held by one hand (left or right) by gripping around the housing 131 and the actuation lever 133. The housing 131 comprises a slider 134 and a spring 135 (explained further below) and the actuation lever 133 is in one embodiment provided with a finger grip 136 to enable safe and precise handling of the laparoscopic device 110.

Figure 20:
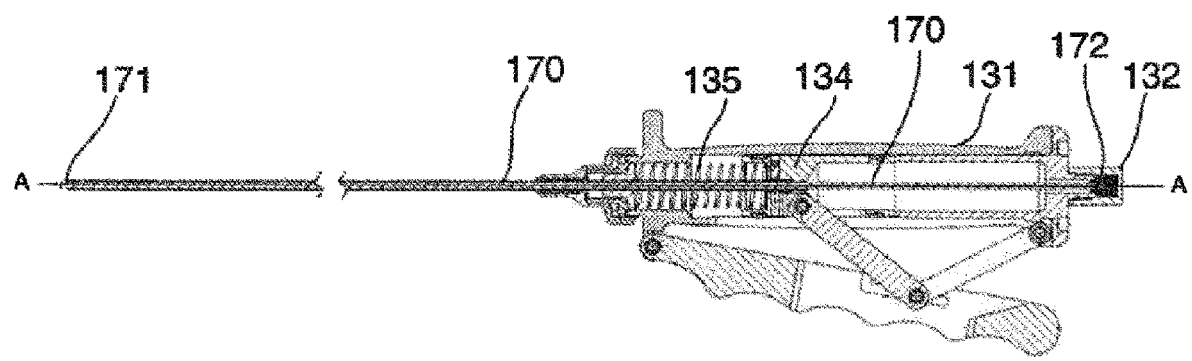
FIG. 20 is a cross sectional view of the laparoscopic instrument including the distal end of the gripping assembly

The tool gripping assembly 160 comprises a longitudinally extending rod 170 having a longitudinal axis A, a distal end 171 and a proximal end 172 (see FIG. 20). The proximal end 172 is configured to be attached to the handle assembly 130. The longitudinal axis A extends along the longitudinally extending rod 170. The longitudinally extending rod distal end 171 is provided with one or more holding members 173 (see FIGS. 21A, and 29A, B, C), each one capable of holding a tool member 120. Each holding member 173 is shaped as a hook comprising a cleft 174 into which the tool member may 120 fit (see FIG. 21A). The clefts 174 may have varying depths. In some embodiments the clefts 174 may be shallow providing only a narrow ledge 175 that will retain the tool member 120 (see FIG. 21B). In other embodiments the clefts 174 may be flat (see FIG. 21C).

Figure 29A:
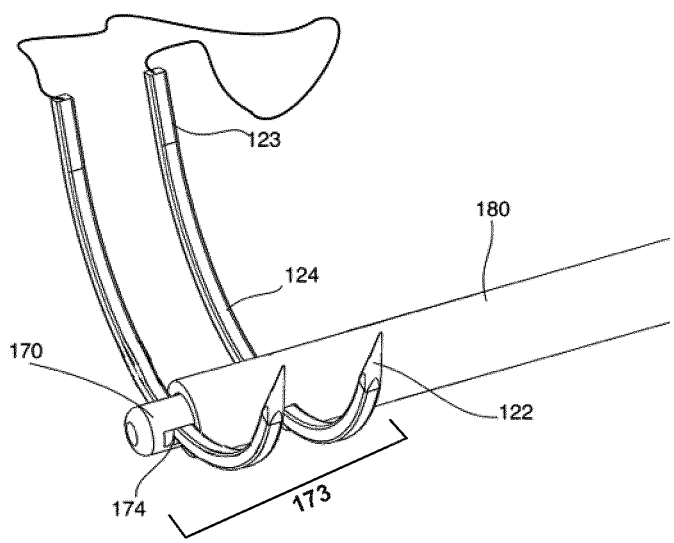
FIGS. 29A-C are views showing an embodiment with two parallel tool members (A) and the holding members for the two tool members in a clamping mode (B) and in a relaxed mode (C).
Figure 29B:
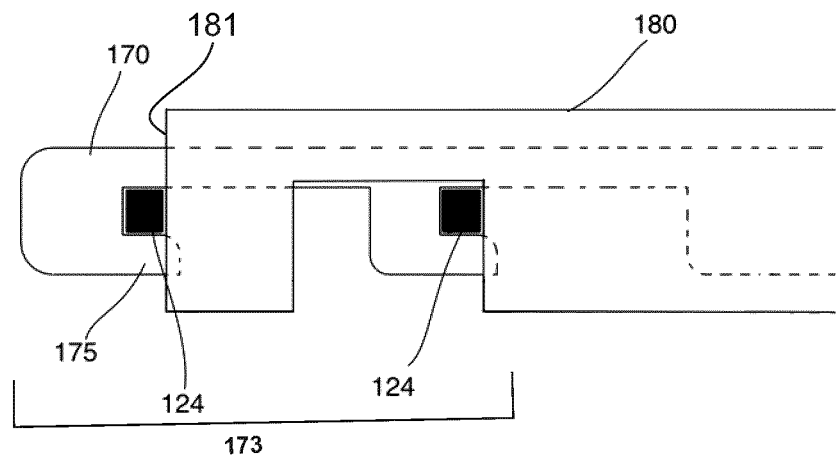
Figure 29C:
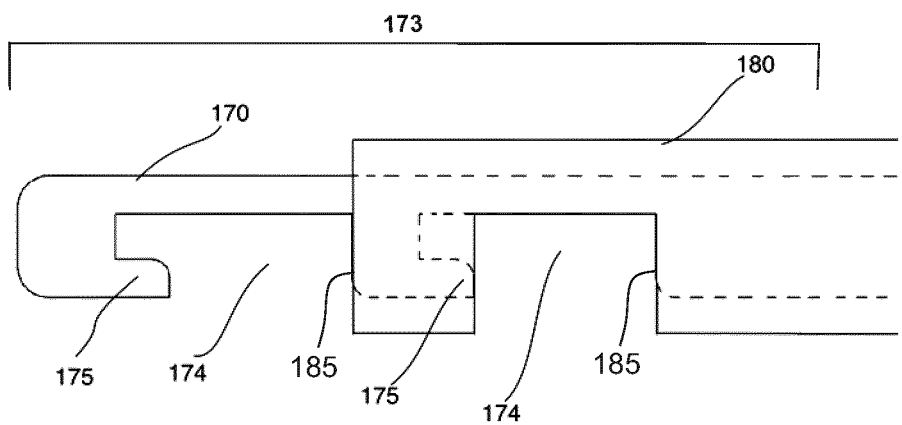

In the illustrations the one or more tool members 120 is a curved suture needle having a first end provided with a piercing tip 122, a second end 123 opposite the first end, and a mid-portion 124 (as illustrated in FIGS. 18 and 29A). In one embodiment the mid-portion 124 of the tool member 120 has a square or rectangular cross section configured to fit into the one or more clefts 174 of the holding members 173 at the longitudinally extending rod distal end 171 (see FIGS. 21A, B and 29B and C. A square or rectangular cross section prevents rotation of the tool members 120 when clamped against the holding members 173.

The longitudinally extending rod 170 extends from the distal end 171 of the laparoscopic device 110, through the entire handle assembly 130 (see FIG. 20). At its proximal end 172 it is attached to a nut 132 arranged on the exterior of the handle assembly 130.

Figure 21A:
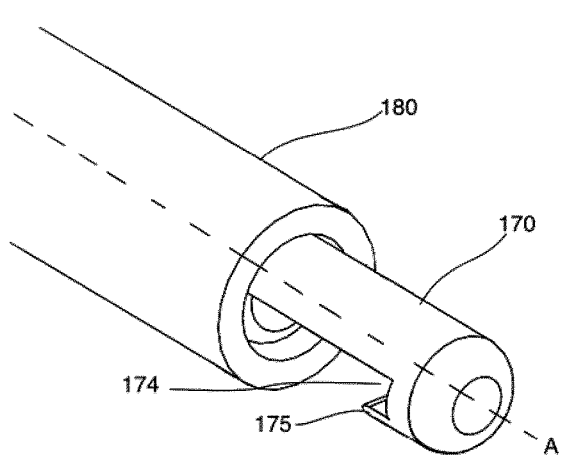
FIGS. 21A-C are detailed views of the holding members at the distal end of the longitudinally extending rod.
Figure 21B:
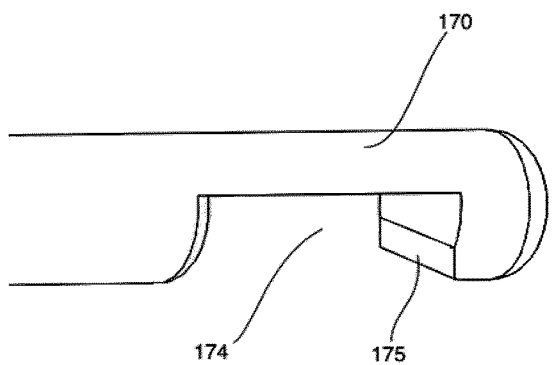
Figure 21C:
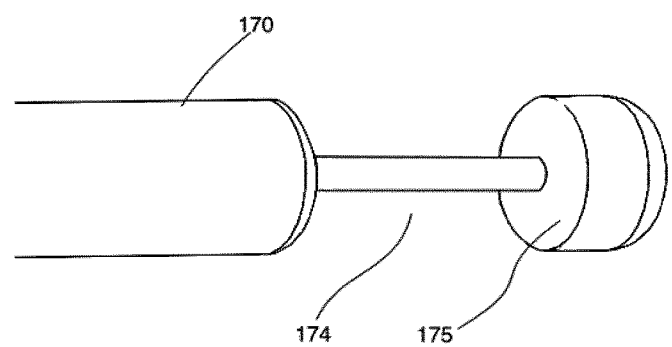

The tool gripping assembly 160 further comprises a sleeve 180 partially surrounding and being longitudinally and independently displaceable parallel to the longitudinal axis A along an outer surface of said longitudinally extending rod 170 (see FIG. 21A). The sleeve 180 has an extension in its longitudinal direction which substantially exceeds its extension in the transverse direction. The longitudinal extension of the sleeve 180 is at least 5 times, at least 10 times, such as more than 15 times longer than its transverse extension.

Figure 22:
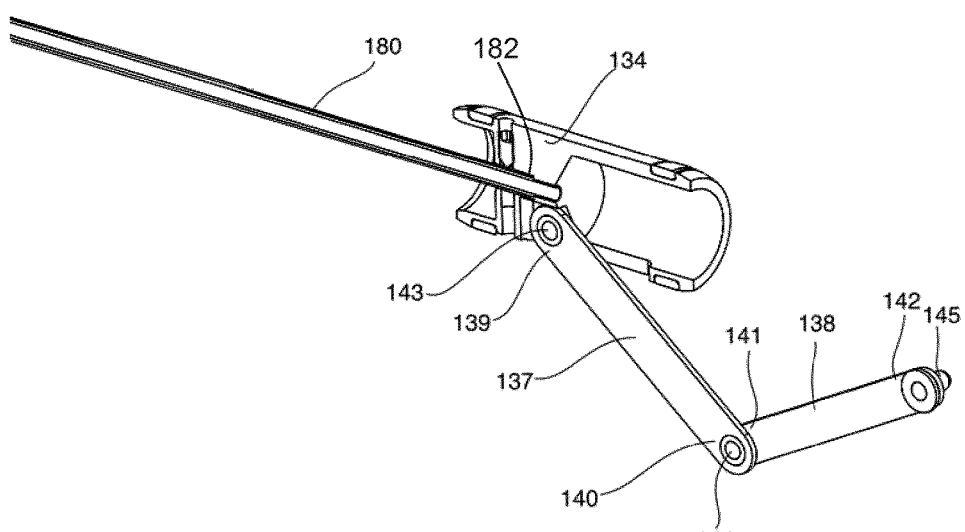
FIG. 22 is a detailed view of the housing showing the proximal end of the longitudinally extending rod when connected to the slider.
Figure 23A:
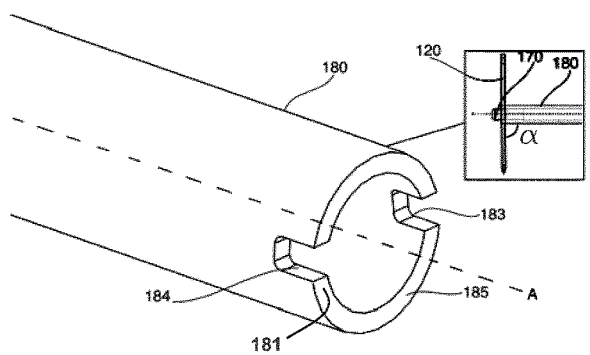
FIGS. 23A and B are detailed views of the notches at the distal end of the sleeve

The sleeve 180 has a distal end 181 and a proximal end 182. The proximal end 182 of the sleeve 180 is attached to the slider 134 inside the housing 131 (see FIG. 22) of the handle assembly 130 as explained further below. The distal end 181 is provided with one or more notches 183 and 184 having different lengths extending parallel to the longitudinal axis A (see FIGS. 23A and B).

Figure 24:
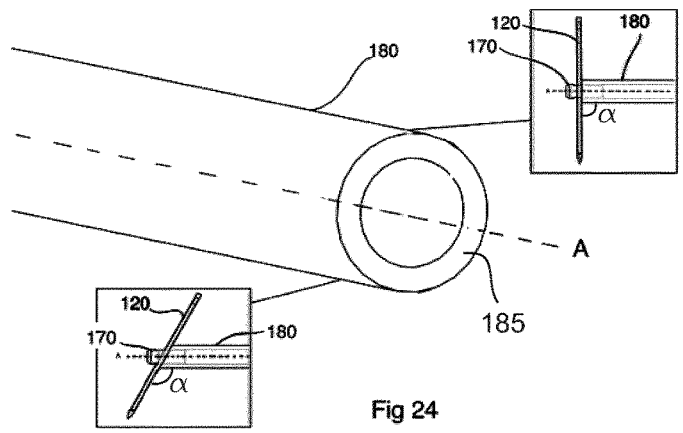
FIG. 24 is a detailed view of an alternative distal end having an edge cut at an angle

The one or more notches 183, 184 may have different lengths and said lengths are configured to abut and clamp said one or more tool members 120 to said one or more holding members 173 at a fixed angle δ in relation to said longitudinal axis A. In one embodiment the widths of the two or more notches 183, 184 match the widths of the square or rectangular cross sections at the tool member mid-portions 124 (see FIGS. 23A, B). In some embodiments the widths of the one or more notches 183, 184 extend around substantially half of the first sleeve 180 circumference. In a further embodiment the distal end of the sleeve 180 is just an edge 185 cut at an angle δ without notches and said edge 185 is configured to abut and clamp said one or more tool members 120 to said one or more holding members 173 at a fixed angle δ in relation to said longitudinal axis A (see FIG. 24).

Figure 25:
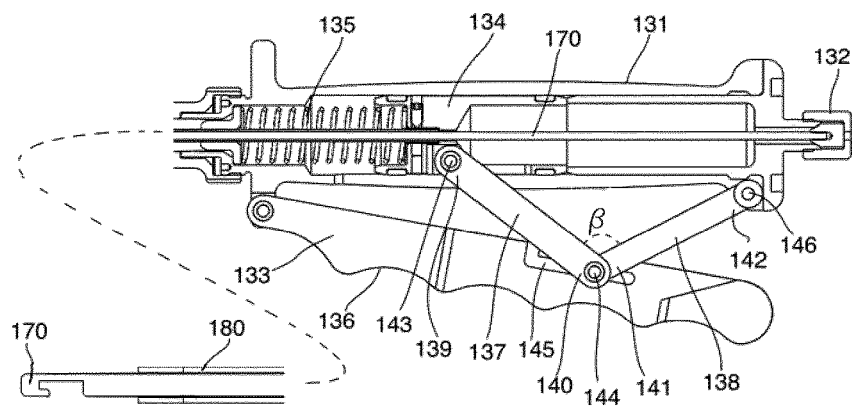
FIG. 25 is a cross sectional view of the alternative laparoscopic instrument in a relaxed mode

The actuation lever 133 which forms part of the handle assembly 130 is articulated to the sleeve 180 via a first and a second linking arm 137, 138 and a slider 134 (see FIGS. 20, and 25). Said first and second linking arms 137, 138 each have a first and a second end 139, 140, 141, 142, wherein the first end 139 of the first linking arm 137 is rotatably connected to the slider 134 located inside the housing 131. The first end 139 of the first linking arm 137 is mounted to the slider 134 by means of a first mounting pin 143 around which the first end 139 of the first linking arm 137 may rotate. The first and second linking arms 137, 138 are connected to each other by means of a sliding pin 144 slidably coupled in an actuation lever slit 145 on the actuation lever 133. The second end 142 of the second linking arm 138 is rotatably connected to the housing 131 by means of a second mounting pin 146 around which the second end 142 of the second linking arm 138 may rotate.

When not in use the laparoscopic device 110 is in a relaxed mode. In the relaxed mode the second end 140 of the first linking arm 137 is connected to the first end 141 of the second linking arm 138 forming a slightly obtuse angle β between the first and second linking arms 137, 138 (see FIG. 25). In the relaxed mode the sleeve 180 has been displaced in the proximal direction from the one or more holding members 173 leaving the one or more clefts 174 in an open position arranged to receive one or more tool members 120 (see small insert in FIG. 25).

Figure 26:
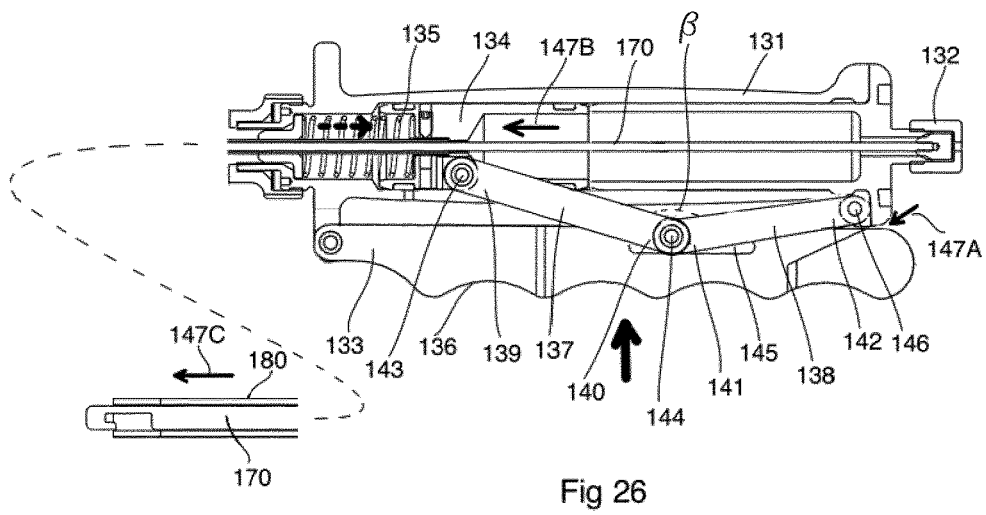
FIG. 26 is a cross sectional view of the alternative laparoscopic instrument in a tool clamping mode
Figure 27:
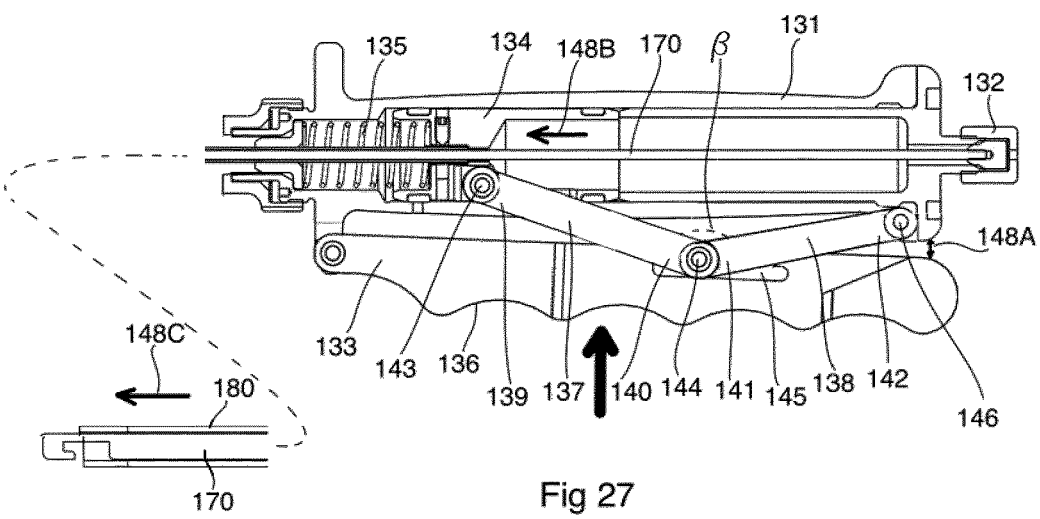
FIG. 27 is a cross sectional view of the alternative laparoscopic instrument in a tool rotating view mode FIG. 28 discloses how the longitudinally extending rod is rotated in the tool rotating mode

However, when a user of the laparoscopic device 110 presses the actuation lever 133 towards the housing 131 the actuation lever 133 may reach two different working modes; the tool clamping mode (FIG. 26) and the tool rotating mode (FIGS. 26 and 27).

The tool clamping mode is reached when the actuation lever 133 is pressed all the way towards the housing 131 (see arrow 147A in FIG. 26). In this mode the sliding pin 144 slides towards the distal end of the handle assembly 130, increasing the obtuse angle β between the first and second linking arms 137, 138, and thereby pushing the slider 134 towards the distal end of the handle assembly 130 (see arrow 147B in FIG. 26). The slider 134 is resiliently biased towards the proximal end of the housing 131 by means of a spring 135 (see dashed arrow in FIG. 26). In the tool clamping position the actuation lever 133 is configured to slidably displace the sleeve 180 parallel to the longitudinal axis A along the longitudinally extending rod 170 (see arrow 147B in FIG. 26) and firmly clamp the one or more tool members 120 into said one or more holding members 173 (see arrow 147C in FIG. 26).

The resilient spring 135 provides an opposing force (see dashed arrow in FIG. 26) when the actuation lever 133 is pressed towards the housing 131 and consequently the sleeve 180 moves in the proximal direction towards the handle assembly 130 along the longitudinally extending rod 170 and parallel to the longitudinal axis A when the actuation lever 133 is released.

Figure 28:
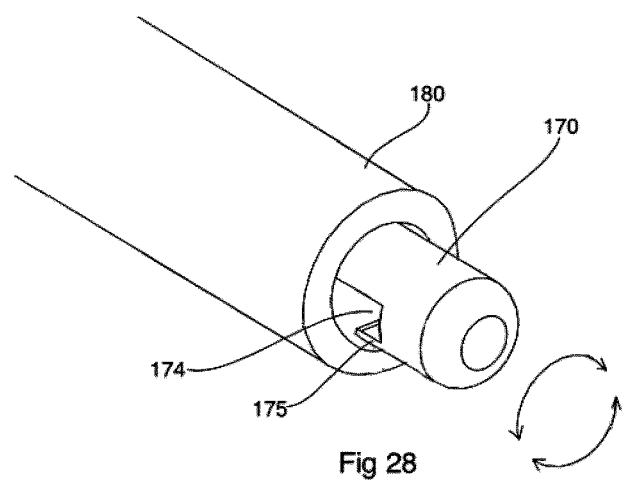

The tool rotating mode is reached when the actuation lever 133 is pressed only half the distance or less towards the housing 131 (see arrow 148A in FIG. 27). The sliding pin 144 slides towards the proximal end of the handle assembly 130, increasing the obtuse angle β between the first and second linking arms 137, 138. In the tool rotating mode the longitudinally extending rod 170 may be rotated around the longitudinal axis A in both the clockwise and the counter clockwise direction (see FIG. 28). Rotation of the longitudinally extending rod 170 rotates also the one or more tool members 120 which are clamped in the holding members 173 thereby enabling the user to place the one or more tool members 120 in the optimal position at the surgical site in relation to the handle assembly 130. This may be very advantageous when for example the operator wants to change position of the first end of the tool member 180° (i.e. flip the tool member to point in the opposite direction). By using the laparoscopic device 110 as described herein this may be achieved without the use of any further tools.

In one embodiment the laparoscopic device 110 may hold two tool members in parallel. In this embodiment the distal end of the sleeve 180 is provided with two notches 183, 184 having distal edges 185 cut at an angle δ. The one or more notches 183, 184 are configured to receive the mid-portions 124 of the one or more tool members 120. Each notch 183, 184 has a length extending parallel to the longitudinal axis A. In another embodiment the widths of the one or more notches 183, 184 extend around substantially half of the circumference of the sleeve 180 (not shown).

The distal edges 185 of the one or more notches 183, 184 are cut at an angle δ such that when said distal edge 185 abut the mid-portion 124 of the one or more tool members 120 to the clefts 174, the one or more tool members 120 are clamped at a fixed angle δ parallel to the cut distal edges 185 of the one or more notches 183, 184.

In one embodiment the distal end 171 of the longitudinally extending rod 170 may be provided with only one holding member 173 capable of holding one tool member 120 at a fixed angle δ. In this embodiment it is the angle δ of the cut edge 185 which will determine the angle of the tool member 120 in relation to the handle assembly 130 (see FIG. 24). This is an advantage when the user is performing surgery at special sites inside the body. For example the site may require that the tool member is held at an angle δ of e.g. 60°, 90°, 120° or the angle which is required in relation to the handle assembly 130. In this case the operator may use a laparoscopic device wherein the edge 185 of the sleeve 180 is cut at the required angle δ. This ensures that the tool member is always held at angle δ relative to the handle assembly.

Figure 23B:
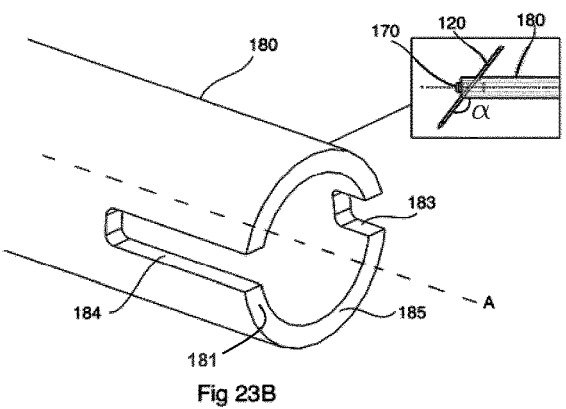

In a further embodiment the distal end 181 may be provided with one or more notches 183, 184 of different lengths (see FIG. 23B. In this embodiment the mid portions 124 of the tool members 120 are clamped inside he notches 183, 184 of different lengths against the clefts 174 of the tool holding members 173. The tool members 120 are held at a fixed angle in relation to said longitudinal axis A A great advantage of the laparoscopic device 110 of the invention is that the tool member 120 may be released and gripped continuously without the use of further tools. This is enabled by using the gripping function of the sleeve 180 as explained above.

Figure 30A:
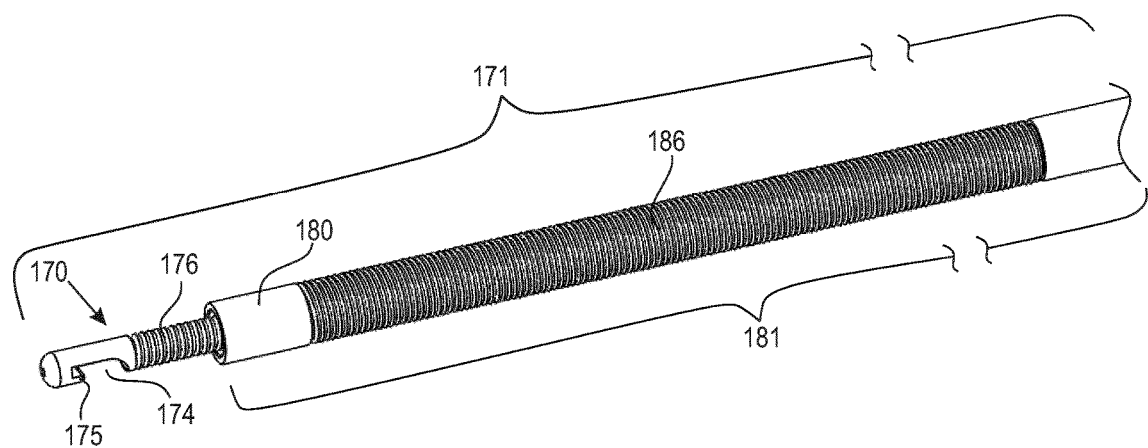
FIGS. 30A and B are views (B cross sectional view) showing an embodiment wherein the distal end of the laparoscopic device is flexible.
Figure 30B:
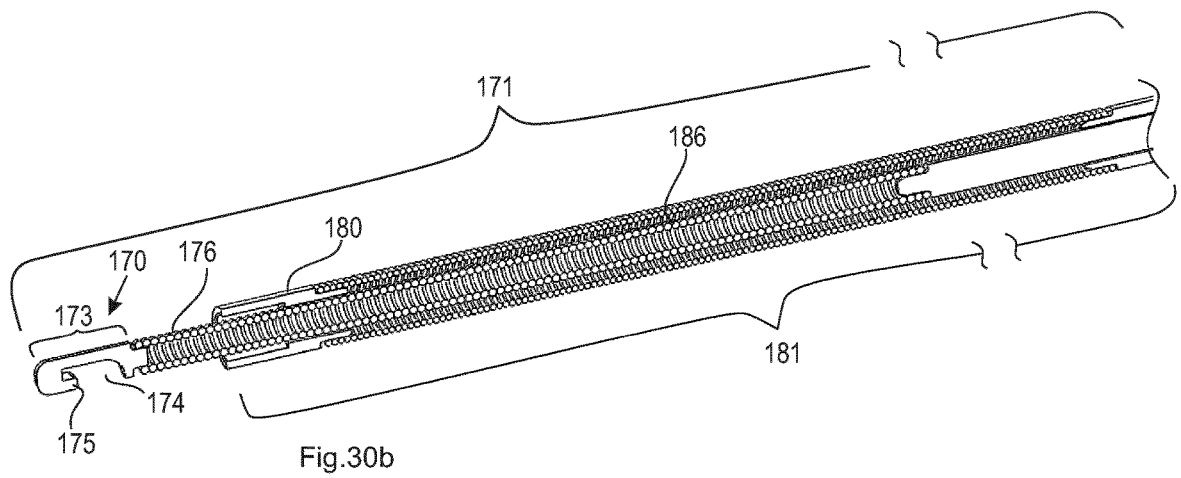

In one embodiment about 5-15 cm at the distal end of the laparoscopic device 10 may be flexible, such that when the operator pushes the distal end against tissue the distal end will bend or flex away from the longitudinal axis A. In this embodiment 5-15 cm of the distal end 171 at the longitudinally extending rod 170 is a spiral wire 176 that may flex (see FIGS. 30A and B). Also the sleeve 180 is provided with a 5-15 cm spiral sleeve 186 at the distal end 181 which enables the sleeve 180 to flex together with the longitudinally extending rod 170 upon pressure. As can be seen in the FIGS. 30A and B it is only the distal end such as 5-15 cm of the laparoscopic device that may flex. The remainder of the longitudinally extending rod 170 and the sleeve 180 are stiff and will not flex or bend. A flexible distal end facilitates reaching with the distal end of the instrument holding a suturing thread or a needle into narrow locations during surgery.

In a further embodiment the distal end of the longitudinally extending rod 170 is provided with two holding members 173 capable of holding two tool members 120 at a fixed angle δ (see FIG. 29A). As explained above it is the angle δ of the cut edges 185 at the distal end that will determine the angle of the tool members 120 in relation to the handle assemble 130.

Figure 31A:
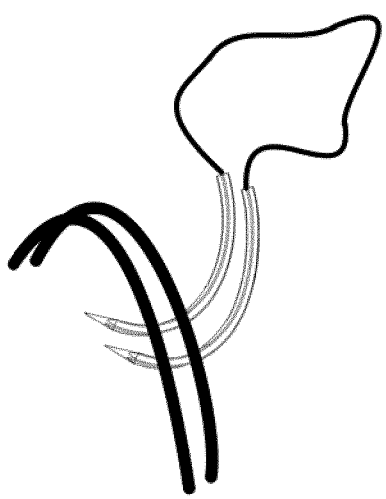
FIGS. 31A-E show how a laparoscopic instrument provided with two parallel suturing needles may be used to suture two adjacent tissues together.
Figure 31B:
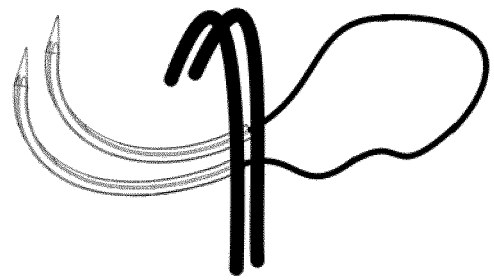
Figure 31C:
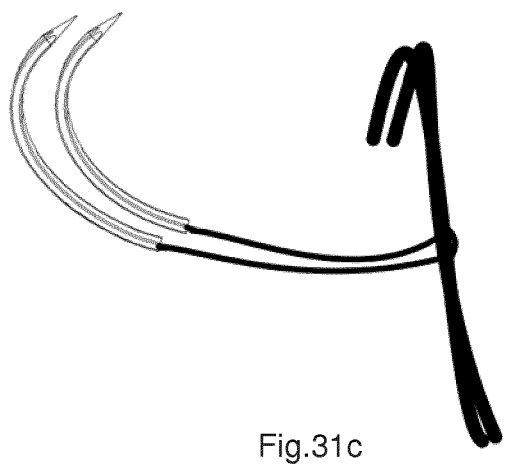
Figure 31D:
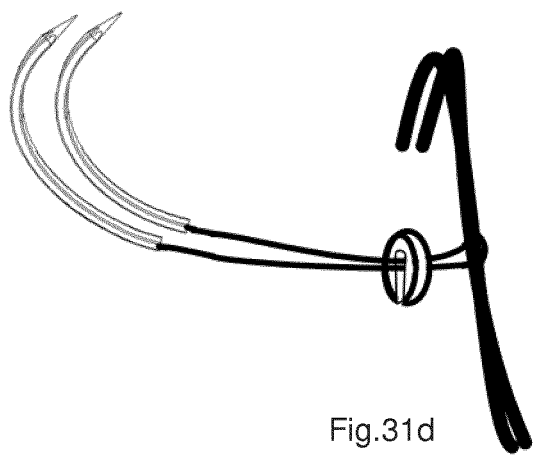
Figure 31E:
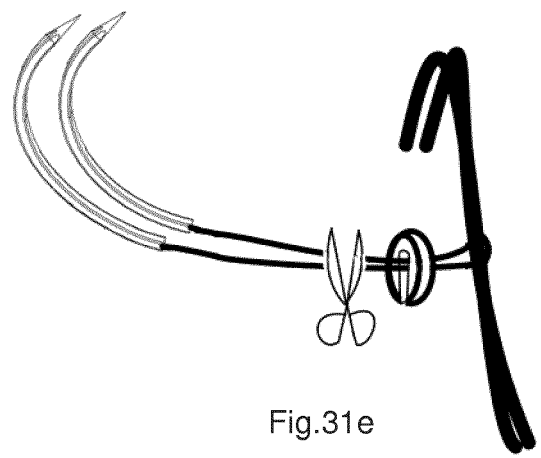

The double needle embodiment may be used when stitching or closing off blood vessels 126 or when suturing two tissues together (see FIGS. 31A-E). In this embodiment the tool members 120 are two suturing needles connected at their second ends 123 by a suturing thread 125. The two needles 120 are pushed through the two layers of tissues to be sutured together, such that one needle ends up at each side of the two tissues (FIGS. 31A-C). The needles 120 are pushed all the way through the tissue. A clip 127 may be used to fasten the thread in a tight grip around the tissue edges 126 (FIG. 31D) and the suturing thread may be cut (FIG. 31E).

The invention claimed is:

1. A laparoscopic device comprising
    a handle assembly by which the user may hold the laparoscopic device; and
    a tool gripping assembly which holds a tool member;
    said tool gripping assembly comprising
    a longitudinally extending rod having a longitudinal axis A, a distal end and a proximal end, said proximal end is configured to be attached to the handle assembly, said distal end is provided with a holding member capable of holding a tool member; and
    a first sleeve partially surrounding and being longitudinally and independently displaceable parallel to the longitudinal axis A along an outer surface of said longitudinally extending rod; and
    a second sleeve partially surrounding and being longitudinally and independently displaceable parallel to the longitudinal axis A along an outer surface of said first sleeve, wherein
    said first and second sleeves are longitudinally displaceable in relation to each other and said longitudinally extending rod, and are configured to clamp said tool member to said holding member in a variable angle α in relation to said longitudinal axis A, wherein said variable angle α depends on the relative positions of the first and second sleeves to the longitudinally extending rod, and
    wherein said handle assembly comprises
    a housing having a sprint and a slider; and
    an actuation lever; wherein
    said actuation lever has four operating modes; the resting mode, the tool clamping mode, the tool rotating mode and the tool angle adjusting mode.

2. The laparoscopic device according to claim 1, wherein said tool member is a suture needle having a first end provided with a piercing tip, a second end opposite to the first end and a mid-portion having a square cross section.

3. The laparoscopic device according to claim 1, wherein said actuation lever is articulated to the first and second sleeves via a first and a second linking arm and said slider, said first and second linking arms each have a first and a second end, and wherein the first end of the first linkage arm is connected to the slider (34), the second end of the first linkage arm is connected to the first end of the second linkage arm by means of a sliding pin slidably coupled to an actuation lever slit arranged in the actuation lever, and the second end of the second linkage arm is connected to the housing.

4. The laparoscopic device according to claim 1, wherein in the tool rotating mode the longitudinally extending rod may be rotated around the longitudinal axis A in both the clockwise and the counter clockwise direction.

5. The laparoscopic device according to claim 1, wherein in the tool clamping mode the actuation lever is configured to slidably displace the first and second sleeves simultaneously and parallel to the longitudinal axis A and along the longitudinally extending rod.

6. The laparoscopic device according to claim 1, wherein in the tool angle adjusting mode a tool angle adjusting assembly is configured to slidably displace the second sleeve parallel to the longitudinal axis A in relation to the first sleeve and the longitudinally extending rod when a second tool angle adjusting member of the tool angle adjusting assembly is rotated.

7. The laparoscopic device according to claim 6, wherein said first sleeve has a distal end and a proximal end, said proximal end is configured to be attached to the handle assembly, and said distal end is provided with a first notch configured to receive and abut the mid-portion of the tool member.

8. The laparoscopic device according to claim 6, wherein said second sleeve has a distal end and a proximal end, said proximal end is configured to be attached to the tool angle adjusting assembly, said distal end is provided with a second notch and a third notch, said second and third notches are configured to receive and abut the mid-portion of the tool member, said second notch is positioned opposite said third notch along a circumference of the second sleeve.

9. The laparoscopic device according to claim 8, wherein said second notch on the second sleeve is aligned with the first notch on the first sleeve.

10. The laparoscopic device according to claim 8, wherein said first notch on the first sleeve is longer than the second notch on the second sleeve, and said third notch on the second sleeve is longer than the first notch on the first sleeve.

11. The laparoscopic device according to claim 8, wherein when said tool member is clamped to said holding member by slidably displacing said first and second sleeves longitudinally and parallel to said longitudinal axis A in relation to each other and said longitudinally extending rod, said mid-portion of the tool member is positioned in at least one or more of the first, second and third notches, thereby placing said tool member into varying angles α in relation to said longitudinal axis A.

12. The laparoscopic device according to claim 1, wherein said angle α of the tool member varies between 30° to 150° in relation to said longitudinal axis A.

13. A laparoscopic device comprising
a handle assembly comprising a housing and an actuation lever by which the user may hold the laparoscopic device; and
a tool gripping assembly which holds one or more tool members;
said tool gripping assembly comprising
a longitudinally extending rod having a longitudinal axis A, a distal end and a proximal end, and said proximal end is configured to be attached to the handle assembly, said distal end is provided with one or more holding members capable of holding one or more tool members; and
a sleeve partially surrounding and being longitudinally and independently displaceable parallel to the longitudinal axis A along an outer surface of said longitudinally extending rod; wherein
said sleeve has a distal end provided with one or more notches having edges cut at an angle δ wherein said edges are configured to abut and clamp said one or more tool members to said one or more holding members at a fixed angle δ in relation to said longitudinal axis A, characterized in that said actuation lever has two working positions; the tool rotating position and the tool clamping position, wherein in the tool rotating position the longitudinally extending rod may be rotated around the longitudinal axis A in both the clockwise and the counter clockwise direction; wherein
said housing comprises a sprint and a slider, and said actuation lever is articulated to the sleeve via a first and a second linking arm and the slider, said first and second linking arms each have a first and a second end, and wherein the first end of the first linkage arm is connected to the slider, the second end of the first linkage arm is connected to the first end of the second linkage arm by means of a sliding pin slidably coupled in an actuation lever slit arranged in the actuation lever, and the second end of the second linkage arm is connected to the housing.

14. The laparoscopic device according to claim 13, wherein said one or more tool members is a suture needle having a first end provided with a piercing tip, a second end opposite to the first end, and a mid-portion having a square or rectangular cross section.

15. The laparoscopic device according to claim 13, wherein in the tool clamping position the actuation lever is configured to slidably displace the sleeve parallel to the longitudinal axis A along the longitudinally extending rod and clamp the one or more tool members into said one or more holding members.

16. The laparoscopic device according to claim 13, wherein said sleeve has a proximal end configured to be attached to the handle assembly, and said distal end of the sleeve provided with one or more notches having edges cut at an angle δ are configured to receive and abut the mid-portion of the one or more tool members.

17. The laparoscopic device according to claim 13, wherein said distal end of the longitudinally extending rod is provided with one holding member capable of holding one tool member.

18. The laparoscopic device according to claim 13, wherein said distal end of the longitudinally extending rod is provided with two holding members capable of holding two tool members.

19. The laparoscopic device according to claim 13, wherein said distal end of the laparoscopic device is flexible.

* * * * *